United States Patent
Njoroge et al.

(10) Patent No.: US 9,580,679 B2
(45) Date of Patent: Feb. 28, 2017

(54) METHODS AND DEVICES FOR SAMPLE LYSIS

(71) Applicant: California Institute of Technology, Pasadena, CA (US)

(72) Inventors: Samuel Njoroge, Pasadena, CA (US); John Gorman, Carlsbad, CA (US); George Maltezos, Merrick, NY (US); Axel Scherer, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 14/033,365

(22) Filed: Sep. 20, 2013

(65) Prior Publication Data

US 2014/0087359 A1     Mar. 27, 2014

Related U.S. Application Data

(60) Provisional application No. 61/704,362, filed on Sep. 21, 2012.

(51) Int. Cl.
| | |
|---|---|
| *C12N 1/06* | (2006.01) |
| *B01L 3/00* | (2006.01) |
| *B01L 7/00* | (2006.01) |
| *C12M 1/00* | (2006.01) |

(Continued)

(52) U.S. Cl.
CPC ............... *C12M 47/06* (2013.01); *C12N 1/06* (2013.01); *C12N 1/066* (2013.01); *B01L 3/5027* (2013.01); *B01L 7/52* (2013.01); *B01L 2300/1883* (2013.01); *C12M 21/00* (2013.01); *G01N 27/44791* (2013.01)

(58) Field of Classification Search
CPC ............ C12M 47/06; C12M 1/00; C12N 1/06; C12N 1/066; G01N 27/44791; B01L 7/52; B01L 3/5027; B01L 2300/1883
See application file for complete search history.

(56) References Cited

U.S. PATENT DOCUMENTS

| | | |
|---|---|---|
| 5,017,998 A | 5/1991 | Miura et al. |
| 5,418,365 A | 5/1995 | Robin et al. |
| 5,856,174 A | 1/1999 | Lipshutz et al. |

(Continued)

FOREIGN PATENT DOCUMENTS

| | | |
|---|---|---|
| WO | WO 00/70082 A1 | 11/2000 |

OTHER PUBLICATIONS

Beckers, et al. Mechanical Cell Lysis Device. 14th Internation Conference on Miniaturized Systems for Chemistry and Life Sciences. Oct. 3-7, 2010, Groningen, The Netherlands. pp. 85-87.

(Continued)

*Primary Examiner* — Jennifer Wecker
(74) *Attorney, Agent, or Firm* — Steinfl + Bruno, LLP

(57) ABSTRACT

Disclosed herein are methods and systems for use in preparing a sample. The methods and systems may be used for lysing one or more structures in a sample (e.g., cells, viral particles, etc.). The methods and compositions may comprise a microfluidic chip or use thereof. The microfluidic chips disclosed herein may comprise (a) a substrate comprising a chamber, wherein at least one mechanical element may be located within the chamber; (b) a thermal element in contact with the chamber; and (c) at least one aperture within the surface of the substrate, wherein the aperture may be configured to insulate the chamber.

24 Claims, 17 Drawing Sheets

(51) Int. Cl.
  *B01J 19/24* (2006.01)
  *G01N 27/447* (2006.01)

(56) References Cited

U.S. PATENT DOCUMENTS

| | | | |
|---|---|---|---|
| 6,068,751 A * | 5/2000 | Neukermans | 204/601 |
| 6,287,831 B1 | 9/2001 | Tai et al. | |
| 7,169,277 B2 | 1/2007 | Ausserer et al. | |
| 8,304,185 B2 | 11/2012 | Stone | |
| 8,313,906 B2 | 11/2012 | Cao et al. | |
| 8,404,440 B2 | 3/2013 | Solli et al. | |
| 8,435,465 B2 | 5/2013 | Sundaram et al. | |
| 2004/0058423 A1 | 3/2004 | Albritton et al. | |
| 2004/0144169 A1* | 7/2004 | Popielas | G01F 1/692 73/200 |
| 2004/0151629 A1* | 8/2004 | Pease | B01L 3/5027 422/68.1 |
| 2004/0229295 A1* | 11/2004 | Marchitto et al. | 435/7.5 |
| 2005/0031795 A1* | 2/2005 | Chaudhury et al. | 427/535 |
| 2005/0064598 A1 | 3/2005 | Yuan et al. | |
| 2005/0112754 A1* | 5/2005 | Yoon et al. | 435/287.2 |
| 2006/0251553 A1* | 11/2006 | Iordanov | B01L 3/50851 422/600 |
| 2007/0134809 A1 | 6/2007 | Cho et al. | |
| 2008/0000892 A1* | 1/2008 | Hirano | B01L 3/50851 219/433 |
| 2010/0068781 A1 | 3/2010 | Rajagopal et al. | |
| 2010/0112667 A1 | 5/2010 | Sundaram et al. | |
| 2010/0291611 A1* | 11/2010 | Bolbot et al. | 435/29 |
| 2011/0005932 A1* | 1/2011 | Jovanovich et al. | 204/453 |
| 2011/0020459 A1 | 1/2011 | Achrol et al. | |
| 2011/0045993 A1* | 2/2011 | Kent | B01L 3/502776 506/7 |
| 2011/0151498 A1 | 6/2011 | Quake et al. | |
| 2011/0312713 A1* | 12/2011 | Azimi | B01L 3/5027 506/39 |
| 2012/0091235 A1 | 4/2012 | Li et al. | |
| 2012/0175441 A1 | 7/2012 | Rajagopal et al. | |
| 2012/0231466 A1 | 9/2012 | Kelso et al. | |
| 2012/0309004 A1 | 12/2012 | Hwang et al. | |
| 2013/0078155 A1* | 3/2013 | Jones et al. | 422/119 |
| 2013/0137105 A1* | 5/2013 | Zhang | C12P 19/34 435/6.12 |
| 2013/0157274 A1 | 6/2013 | Belgrader et al. | |
| 2013/0164754 A1 | 6/2013 | Malik et al. | |
| 2013/0217022 A1 | 8/2013 | Cao et al. | |
| 2013/0331298 A1* | 12/2013 | Rea | 506/16 |

OTHER PUBLICATIONS

Kim, et al. Microfluidic sample preparation: cell lysis and nucleic acid purification Integr Biol (Camb). Oct. 2009;1(10):574-86. doi: 10.1039/b905844c. Epub Aug. 25, 2009.

Lee, et al. Electrochemical cell lysis device for DNA extraction. Lab Chip. Mar. 7, 2010;10(5):626-33. doi: 10.1039/b916606h. Epub Dec. 17, 2009.

Shah, et al. A novel passive microfluidic device for preprocessing whole blood for point of care diagnostics. International Solid-State Sensors, Actuators and Microsystems Conference. 2009; 417-420.

International search report and written opinion dated Apr. 17, 2014 for PCT Application No. US2013/061063.

* cited by examiner

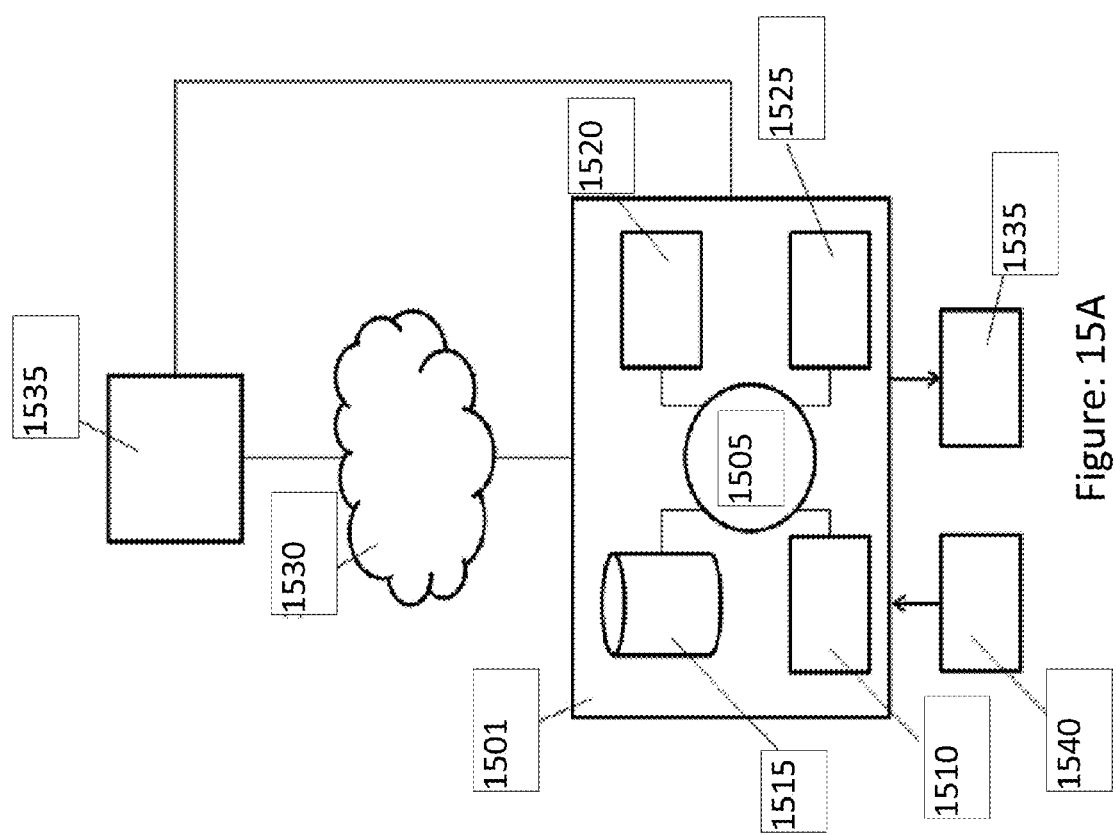

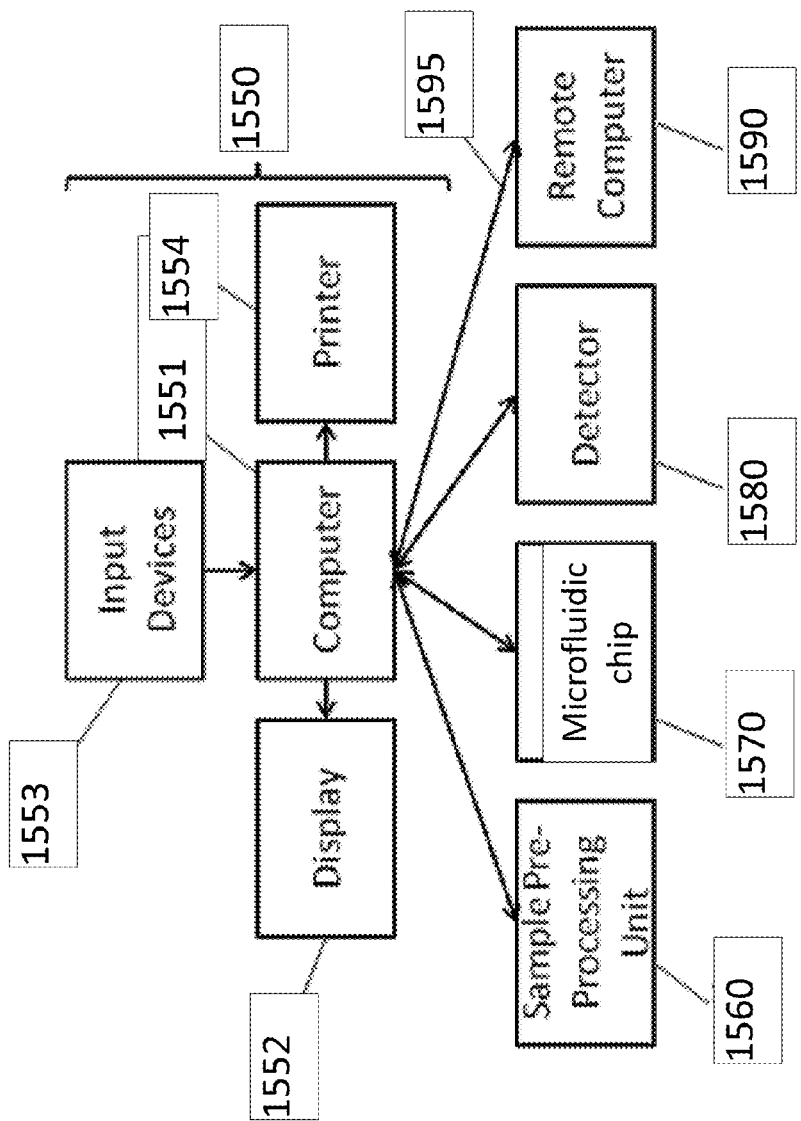
Figure: 15B

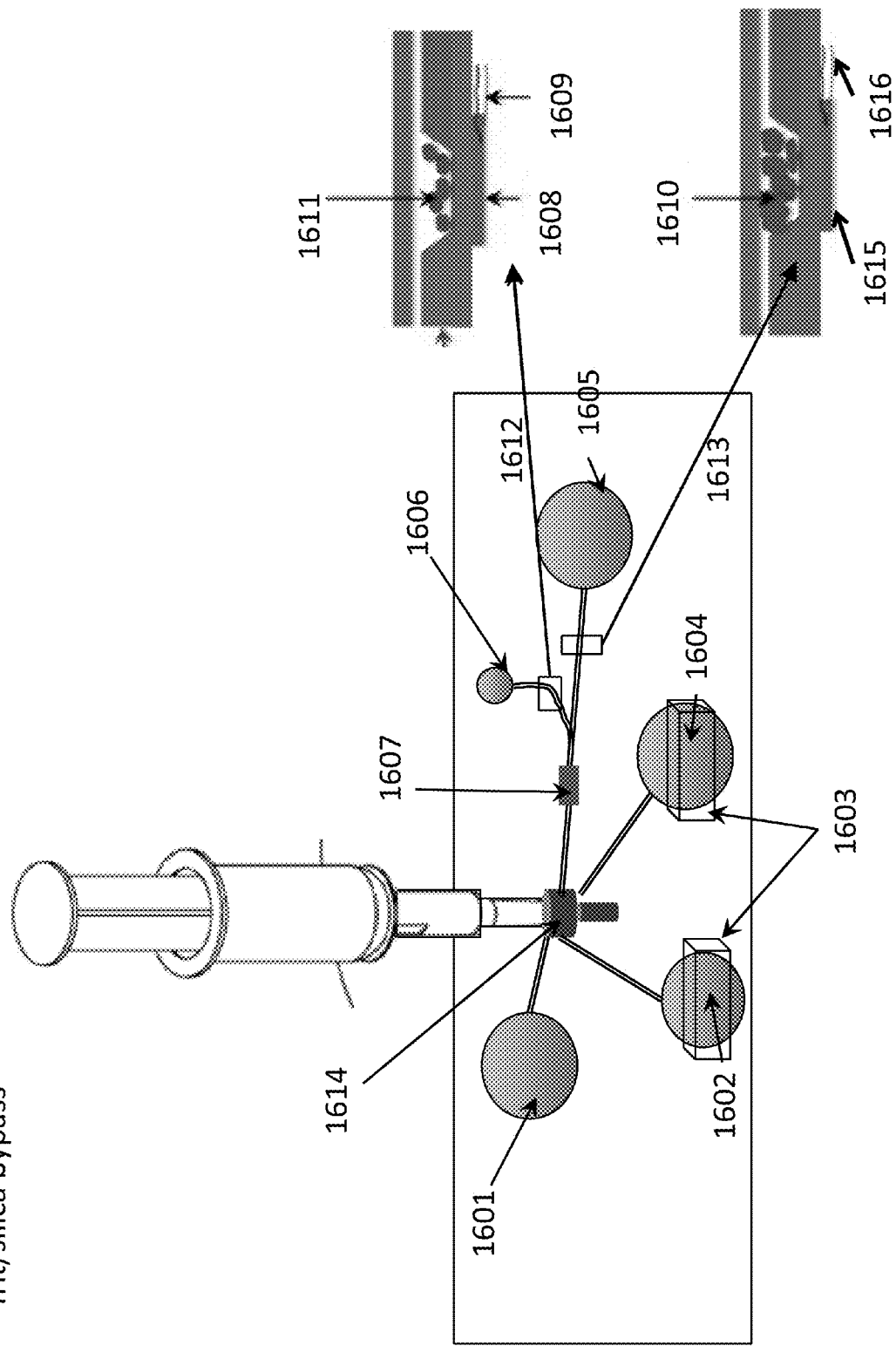
Figure 16: Glass frit/silica bypass

METHODS AND DEVICES FOR SAMPLE LYSIS

CROSS-REFERENCE

This application claims the benefit of U.S. Provisional Application No. 61/704,362, filed Sep. 21, 2012, which application is incorporated herein by reference in its entirety for all purposes.

BACKGROUND OF THE INVENTION

Cell lysis can involve the destruction, or disruption, of a cell's membrane or wall, which breaks open the cell and exposes its contents. Many techniques are available for the disruption of cells, including physical, chemical (e.g., detergent-based methods, chaotropic salts) and biochemical (e.g., enzymes such as lysozyme). Mechanical lysis, such as vortexing and bead-beating, is also a form of physical lysis. Sonication is another form of physical lysis, which uses pulsed, high frequency sound waves to agitate and lyse cells, bacteria, spores, and finely diced tissue.

SUMMARY OF THE INVENTION

Disclosed herein are methods and systems for use in preparing a sample. The methods and systems may be used for lysing one or more structures in a sample. The methods and compositions may comprise a microfluidic chip or use thereof. The microfluidic chips disclosed herein may comprise (a) a substrate comprising a chamber, wherein at least one mechanical element may be located within the chamber; (b) a thermal element or device in contact with the chamber; and (c) at least one aperture within the surface of the substrate, wherein the aperture may be configured to insulate the chamber.

Disclosed herein are microfluidic chips that may comprise: (a) a substrate comprising a chamber, wherein at least one mechanical element is located within the chamber; (b) a thermal element in contact with the chamber; and (c) at least one aperture within the surface of the substrate, wherein the aperture is configured to insulate the chamber.

A microfluidic chip disclosed herein may comprise a thermal element which is a thermoelectric heater. A microfluidic chip may comprise a thermal element which is a thermoelectric cooler.

A microfluidic chip disclosed herein may comprise at least one aperture configured to insulate a chamber. The at least one aperture may be greater than 0.5 µm in length. The at least one aperture may be up to about 1 mm in length. The at least one aperture may extend from the top of the substrate to the bottom of the substrate in order to permit the flow of air through the aperture. The at least one aperture may be a depression that extends through at most 95% of a substrate. The at least one aperture may extend around greater than 80% of the perimeter of the chamber. The at least one aperture may be vacuum sealed. The at least one aperture may be filled with an insulative material. The insulative material may comprise silicon dioxide, wool, felt, fiberglass, urethane or combinations thereof. The insulative material may comprise xenon, dichlorodifluoromethane, argon, nitrogen or combinations thereof. The at least one aperture may be at least two apertures. The at least one aperture may be at least nine apertures. The at least two apertures maybe between about 0.05 inches to about 0.100 inches apart.

A microfluidic chip provided herein may comprise a mechanical element. The mechanical element may comprise a stir bar. The mechanical element may comprise a plurality of beads. The mechanical element may comprise an array of electrodes.

The microfluidic chip disclosed herein may comprise a vent. In some cases, the microfluidic chip disclosed herein may comprise a filter.

A microfluidic chip disclosed herein may comprise one or more chambers. A microfluidic chip disclosed herein may comprise a first sample chamber and a second sample chamber, wherein the first and second sample chambers are fluidly connected to the chamber and wherein the ratio of the volume of the first sample chamber to the volume of the second sample chamber is at least 2:1. The length of a cross-section of a chamber may be greater than 3 mm. The volume of a chamber may be at most 25 ul.

A microfluidic chip disclosed herein may comprise a thermal conductor. In some cases, a microfluidic chip disclosed herein may comprise a thermal transducer. In some cases, a microfluidic chip disclosed herein may comprise a thermal sensor.

A microfluidic disclosed herein may comprise a pouch. A pouch may be made of polypropylene (PP), polyethylene (PE), polystyrene (PS), polyethylene terephthalate (PET), polycarbonate (PC), aluminum, nitrocellulose or combinations thereof.

A microfluidic chip disclosed herein may have greater than 50% of the thermal energy within a chamber contained therein. A microfluidic chip disclosed herein may have greater than 60% of the thermal energy within a chamber contained therein. A microfluidic chip disclosed herein may have greater than 70% of the thermal energy within a chamber contained therein.

In some cases, any microfluidic chip disclosed herein may be manufactured by using converted-tape technology.

A microfluidic chip provided here may comprise (a) a substrate comprising a first chamber; and (b) a patterned channel in fluidic contact with the first chamber, wherein i) the interior surface of one or more walls of the patterned channel has a plurality of grooves, and ii) the patterned channel is in contact with at least one thermal element. The at least one thermal element may be in contact with the first chamber. The at least one thermal element may be in contact with the patterned channel. The patterned channel may be between about 1 cm to about 15 cm in length. The patterned channel may be between about 30 µm to about 500 µm in width. The patterned channel may be between about 30 µm to about 250 µm in depth. The plurality of grooves may be etched into the one or more walls of the channel. The plurality of grooves may be staggered. The pattern may be a herringbone pattern. The grooves may be v-shaped, c-shaped, u-shaped, j-shaped, i-shaped, x-shaped, l-shaped or t-shaped. The patterned channel may be configured to perturb the laminar flow of a fluid flowing through the patterned channel. A patterned mixing channel may be in a serpentine shape. The microfluidic chip may further comprise at least one aperture configured to insulate the patterned channel.

The microfluidic chip may comprise an inlet channel connecting a first chamber to the patterned channel, wherein the length of the inlet channel is between about 0.5 cm to about 5 cm and the width of the inlet channel is between about 30 µm to about 100 µm.

A microfluidic chip disclosed herein may comprise: (a) a substrate comprising a first chamber; (b) a first patterned channel in fluidic contact with the first chamber, wherein the first patterned channel comprises a plurality of grooves on the interior surface of one or more walls of the channel; (c)

a second patterned channel fluidly connected to the first chamber, wherein the second patterned channel comprises a plurality of grooves on the interior surface of one or more walls of the channel; and (d) a second chamber fluidly connected to the first and second patterned channels, wherein the second chamber is positioned between the first and second patterned channels. The grooves may be v-shaped, c-shaped, u-shaped, j-shaped, i-shaped, x-shaped, l-shaped or t-shaped. A thermal element may be in thermal contact with the first patterned channel. A thermal element may be thermal contact with the second patterned channel. An array of one or more apertures may be positioned around the first and second patterned channels.

Provided are methods of lysing a sample comprising: (a) introducing a sample into a chamber within a microfluidic device; and (b) lysing the sample by heating the sample within the chamber, wherein the chamber is separated from a portion of the device by at least one insulating aperture. Lysing of the sample may also comprise chemical or mechanical lysis. The insulating aperture may permit air to flow through the microfluidic device, either from top of the microfluidic device to bottom, or from bottom to top. Lysing the sample may further comprise agitating the sample. The sample maybe agitated with a stir bar which maybe located within the chamber. The sample maybe agitated with a plurality of beads within the chamber. The sample maybe agitated with an actuator.

In a method of lysis disclosed herein the chamber maybe heated for between about 1 min to about 10 min. The chamber is heated to at least about 60° C.

A method of lysis disclosed herein may further comprise mixing the sample with one or more reagents. The method of lysing may further comprise lysing a sample by flowing the sample through a patterned channel within a microfluidic device, and providing thermal energy to the sample within the patterned channel. Mixing of the sample and a lysis buffer in the patterned channel may result in lysis of greater than 90% of the sample. A method of lysis disclosed herein may comprise flowing the sample into one or more additional channels. The one or more additional channels maybe patterned channels. The sample maybe flowed through the patterned channel and the one or more additional channels sequentially. The sample maybe flowed through the patterned channel and the one or more additional channels concurrently. The patterned channel may contain one or more reagents.

The method of lysing the sample may further comprise mixing the sample with one or more reagents. The sample may contain a bodily fluid or an extract or derivative thereof. The sample may contain blood, plasma, mucus, feces, urine or combinations thereof. The sample may contain whole blood.

Disclosed are methods of improving efficiency a sample lysis reaction comprising: (a) introducing a sample into a chamber within a microfluidic device; (b) lysing the sample by heating the sample within the chamber, wherein the chamber is separated from a portion of the device by at least one insulating groove, wherein the efficiency of the sample lysis reaction is increased by at least about 10% as compared to a microfluidic device not comprising the at least one insulating groove. The efficiency of the sample lysis reaction maybe based on a comparison of the lysis product or the energy usage. The microfluidic device may use less electricity than a corresponding microfluidic device not comprising the at least one insulating groove.

A method of lysing a sample is provided, comprising: (a) introducing the sample into a capillary tube, wherein the capillary tube is spirally wrapped around a thermal element and wherein the capillary tube comprises lysis reagents; and (b) applying alternating negative and positive pressure to the capillary tube for at least two cycles in order to promote mixing of the sample with the lysis reagents. The lysis reagents maybe in liquid form. The lysis reagents maybe lyophilized. The thermal element may comprise a cartridge heater. The negative and positive pressure maybe applied with a plunger or linear actuator in fluid connection to the capillary tube. The thermal element may comprise a cartridge chiller. The thermal element may be couple to a thermal transducer. The capillary tube maybe made of polymers (such as polyethylene), metals, rubbers, polyetheretherketone (PEEK), fluoropolymer or combinations thereof.

A capillary tube useful in a lysis method disclosed herein maybe fluidly connected to a first input tube and a second input tube at a junction. The sample maybe introduced through the first input tube. A lysis reagent maybe introduced through the second input tube. The ratio of the volume of the second input tube to the volume of the first input tube maybe at least 2:1.

A capillary tube useful in a lysis method disclosed herein may have corrugated ridges on its internal surface. The corrugated ridges may contain alternating small and large patterns.

The methods disclosed herein may comprise heating the sample within the chamber. The sample within the chamber may be heated for at least about 10 seconds. The sample within the chamber may be heated for at least about 20 seconds. The sample within the chamber may be heated for at least about 30 seconds. The sample within the chamber may be heated for at least about 45 seconds. The sample within the chamber may be heated for at least about 1 minute. The sample within the chamber may be heated for at least about 2 minutes. The sample within the chamber may be heated for at least about 3 minutes. The sample within the chamber may be heated for at least about 5 minutes. The sample within the chamber may be heated for less than about 30 minutes. The sample within the chamber may be heated for less than about 25 minutes. The sample within the chamber may be heated for less than about 20 minutes. The sample within the chamber may be heated for less than about 15 minutes. The sample within the chamber may be heated for less than about 12 minutes. The sample within the chamber may be heated for less than about 10 minutes. The sample within the chamber may be heated for between about 10 seconds to about 30 minutes. The sample within the chamber may be heated for between about 20 seconds to about 20 minutes. The sample within the chamber may be heated for between about 30 seconds to about 10 minutes.

The sample within the chamber may be heated to at least about 60° C. The sample within the chamber may be heated to at least about 70° C. The sample within the chamber may be heated to at least about 80° C. The sample within the chamber may be heated to at least about 90° C.

The methods disclosed herein may further comprise cooling the sample within the chamber. The sample may be cooled to less than about 25° C. The sample may be cooled to less than about 4° C. The sample may be cooled to less than about 0° C. The sample may be cooled to less than about −10° C. The sample may be cooled to less than about −20° C. The sample may be cooled to less than about −30° C. The sample may be cooled to less than about −40° C. Cooling the sample within the chamber may comprise freezing the sample within the chamber.

Lysing the sample further may comprise mixing the sample with one or more reagents. The one or more reagents may comprise one or more lysis reagents. The one or more reagents may comprise one or more wash buffers. The one or more reagents may comprise one or more diluents.

The methods disclosed herein may comprise the use of a microfluidic channel comprising one or more herringbone mixing channels. The herringbone mixing channel may be in a serpentine shape.

The methods disclosed herein may further comprise flowing the sample into one or more additional channels. The one or more additional channels are herringbone mixing channels. The sample may be flowed through the herringbone mixing channel and the one or more additional channels sequentially. The sample may be flowed through the herringbone mixing channel and the one or more additional channels concurrently.

The methods disclosed herein may comprise the use of one or more lysis reagents. The lysis reagents may be in liquid form. The lysis reagents may be lyophilized.

The methods disclosed herein may comprise the use of one or more thermal elements. The thermal element may comprise a cartridge heater. The thermal element may comprise a cartridge chiller.

The methods disclosed herein may comprise the use of one or more negative and/or positive pressure. The negative and positive pressure may be applied with a plunger or linear actuator in fluid connection to the capillary tube.

The methods disclosed herein may comprise the use of one or more thermal transducers. The thermal element may be coupled to the thermal transducer.

The methods disclosed herein may comprise the use of one or more tubes. The tube may be made of one or more polymers, metals, elastomers, carbon, and composites thereof.

Disclosed herein are kits for lysing a sample comprising a microfluidic chip disclosed here. A kit may also comprise at least one lysis buffer. A kit may further comprise at least one lyophilized lysis reagent. A kit may further comprise at least one PCR reagent. A kit may also comprise at least one pump which maybe a syringe pump. The kit may comprise a device for sample purification. In some cases, a kit comprises a mechanical element such as a stir bar or beads (e.g., magnetic beads, glass beads).

In some specific embodiments, this disclosure provides a microfluidic chip comprising: (a) a chamber, wherein at least one stir bar is located within the chamber; (b) a thermal device in thermal contact with the chamber; and (c) at least one insulative groove within the surface of the chip, which is configured to insulate the chamber. The stir bar may be composed of magnetic material. In some embodiments, provided herein are microfluidic chips comprising: (a) a chamber, wherein a plurality of granular particles (e.g., beads) is located within the chamber; (b) a thermal device in thermal contact with the chamber; and (c) at least one insulative groove within the surface of the chip, which is configured to insulate the chamber. The granular particles may be made of glass, cubic-zirconium, or magnetic particles.

In some cases, the thermal device is a heater; in some cases, it is a cooler. In some cases, at least one insulative groove is a plurality of grooves (e.g., 9) positioned around the chamber. In some cases, the at least one insulative groove is filled with an insulative material.

In some embodiments, the microfluidic chip is coupled to an external magnetic field. The microfluidic chip may further comprise a vent, a filter, and/or one or more additional chambers. The microfluidic device may also comprise at least one pouch such as a fluidic pouch. The pouch may be made of polypropylene, polyethylene, polyethylene terephthalate (PET) or combinations thereof.

In some cases, provided herein are microfluidic chips comprising: a first chamber; and a herringbone mixer in fluidic contact with the first chamber, wherein the herringbone mixer is in thermal contact with at least one thermal device. The herringbone mixer may be a staggered herringbone mixer.

In some cases, provided herein are microfluidic chips comprising: a first chamber; a first herringbone mixer in fluidic contact with the first chamber; a second chamber fluidly connected to the first herringbone mixer; and a second herringbone mixer fluidly connected to the second chamber, wherein the second chamber is positioned between the first and second herringbone mixers. The microfluidic chip may further comprise a thermal device in thermal contact with the second chamber or the first herringbone mixer.

In some cases, provided herein are methods of lysing a sample comprising: introducing a sample into a chamber within a microfluidic device; and lysing the sample by heating the sample within the chamber, wherein the chamber is separated from a portion of the device by at least one insulative groove. The lysing of the sample may also comprise chemical or mechanical lysis. The lysis may also comprise agitating the sample such as with a stir bar, wherein the stir bar is located within the chamber; or with a plurality of beads. In some cases, agitating the sample is done by applying pressure. In some cases, the lysing the sample further comprises mixing the sample with one or more reagents.

Also provided herein are methods of lysing a sample comprising lysing a sample by flowing the sample through a herringbone mixer within a microfluidic chip, and providing thermal energy to the sample within a chamber in fluidic contact with the herringbone mixer. The herringbone mixer may have a serpentine shape. The method may further comprise flowing the sample through one or more additional herringbone mixers. The lysing may involve mixing the sample (e.g., blood or sputum) with one or more reagents.

Also provided herein are methods of lysing a sample comprising: introducing the sample into tubing, wherein the tubing is spirally wrapped around a heating or cooling cartridge and wherein the tubing comprises lysis reagents; and applying negative and positive pressure cycles to the tubing in order to promote mixing of the sample with the lysis reagents. The negative and positive pressure may be applied with a plunger or linear actuator in fluid connection with the tubing. The heating cartridge may be coupled to a thermal transducer. In some cases, the sidewalls of the tubing contains lyophilized lysis reagents; in some cases, the tubing contains liquid lysis reagents.

INCORPORATION BY REFERENCE

All publications, patents, and patent applications mentioned in this specification are herein incorporated by reference in their entireties for all purposes and to the same extent as if each individual publication, patent, or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 15A is a conceptual schematic of an example computer server.

FIG. 15B is a conceptual schematic of an example control assembly.

FIG. 16 is a depiction of an exemplary microfluidic chip described herein.

DETAILED DESCRIPTION OF THE INVENTION

This disclosure provides methods and compositions for lysis of analytes comprising nucleic-acid-containing structures such as cells, microbes, viruses, bacteria, and/or other particles. Often, the lysis is conducted in a device such as a microfluidic chip described herein by use of at least at least one mechanical element located within the chamber. The methods may include one or more of the following approaches to lysing an analyte: (1) thermal lysis in which temperature (either elevated temperature or a series of freeze-thaw cycles) may be used to disrupt cell membranes or particles, such as viral particles; (2) mechanical lysis in which contact forces may be used to crush, shear, burst, or cut analytes; (3) chemical lysis in which chemicals or enzymes may be used to break down cell membranes or particles, such as viral particles; (4) electrical lysis in which (a) membrane porosity may be induced with a low-strength electric field or (b) complete lysis of the targets may be induced with a stronger field. Methods using other lysis approaches may also be used, for example, sonication and lasers. In certain cases, the methods provided herein use combinations of lysis methods, such as heat and mechanical; heat and chemical; heat and electrical; mechanical and chemical; mechanical and electrical; electrical and chemical; laser and heat; laser and mechanical; etc. In some cases, three or more lysis methods are used. The lysis methods may occur within the same chamber of a device; within different chambers of the same device; within different devices; and in other configurations.

Overview of Lysis Device for Mechanical and Thermal Lysis

Figure 1:
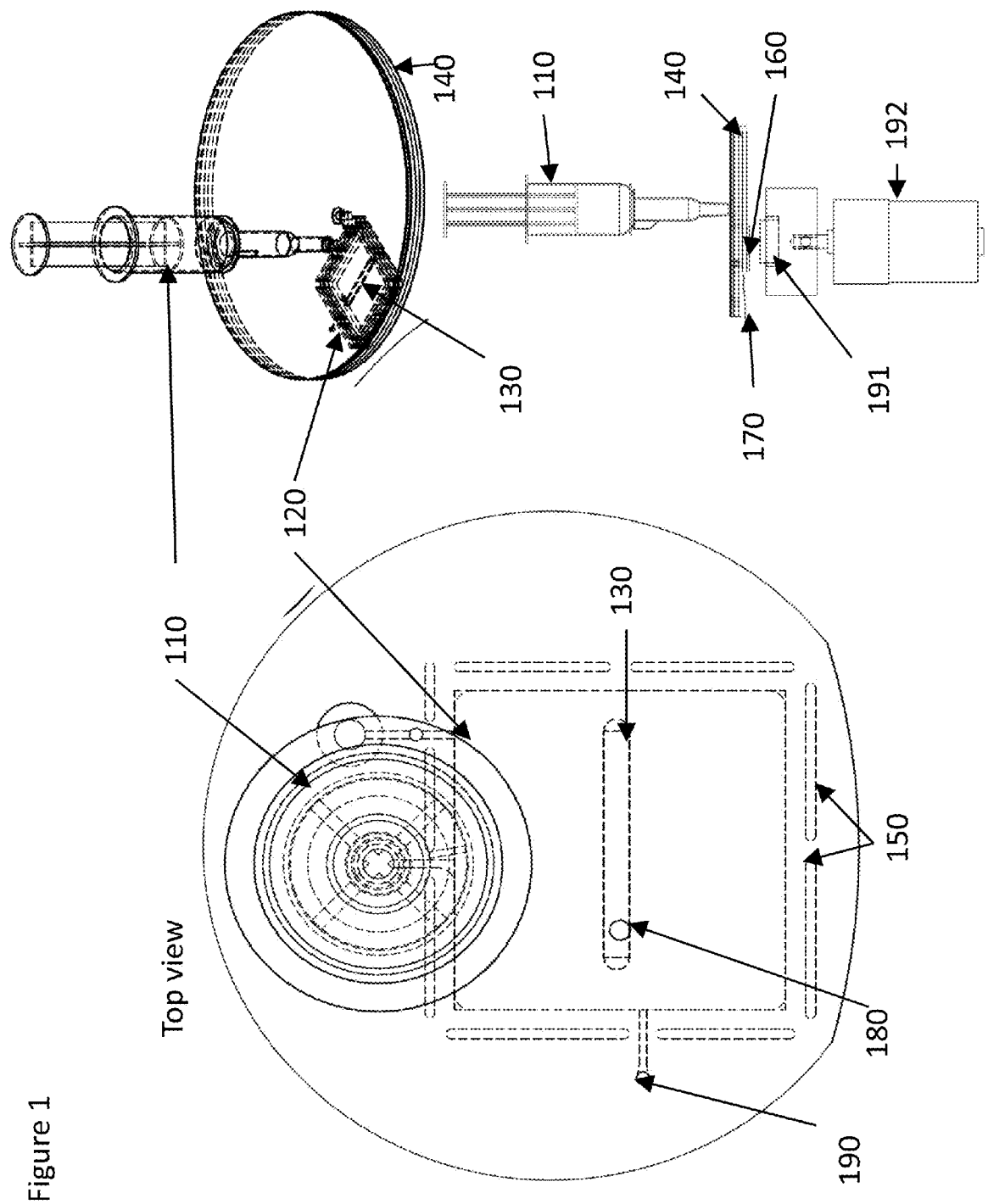
FIG. 1 is a multi-view schematic of an exemplary microfluidic chip described herein, comprising assembled layers with lysis/mixing chambers, heating assembly, thermally insulative grooves, and magnetic stir bar.

FIG. 1 shows a schematic of an exemplary microfluidic chip that can be used to lyse an analyte via mechanical and thermal methods. The microfluidic chip may contain an input port 190 for introducing a sample or reagent into a sample chamber 120. In some cases, the microfluidic chip has a plurality of input ports, such as 2, 3, 4, 5, 6, or more input ports. The microfluidic chip may used for sample lysis and may contain a sample chamber 120 that can be used for lysis and/or mixing. In some cases the microfluidic chip may contain more than one sample chamber, e.g., 2, 3, 4, 5, 6, 7, 8, 9, 10, 25, 50, 96, 100, 200, or more sample chambers. In some cases, the sample chambers have the same function; in some cases they have different functions such as any combination of the following: mixing, lysing, purification, conducting a reaction (e.g., PCR), etc. The sample chamber may be any of a number of shapes and sizes. For example, a cross-section of the sample chamber may be square, circular, semi-circular, oval, elliptical, triangular, rectangular, crescent-shaped, trapezoidal, or other shapes. The sample chamber may be cone-shaped, cyclindrical, cubic, spherical, half-spherical (half-domed), rectangular cuboid (or box-shaped), etc. In some cases, all of the sample chambers are the same size; in some cases, the sample chambers are different sizes. For example, a microfluidic chip of this disclosure may have two sample chambers with volumes with ratios such as 1:2, 1:3, 1:4, 1:5, 1:6, 1:7, 1:8, 1:9, 1:10, 2:3, 2:5, 2:7, 2:9, 3:5, etc. In some cases, a cross-sectional diameter of a sample chamber may be: about 2 mm, 3 mm 4 mm, 5 mm, 5.5 mm, 6 mm, 7 mm, 8 mm, 9 mm, 10 mm, 11 mm, 12 mm, 12.5 mm, 13 mm, 14 mm, or 15 mm. In some cases the sample chamber has a capacity of at least one 1 μl. In some cases the sample chamber has a capacity of up to 750 μl. In some cases the sample chamber has a capacity of at least 5 μl. In some cases the sample chamber has a capacity of at least 10 μl. In some cases the sample chamber has a capacity of at most 10 μl. In some cases the sample chamber has a capacity of at most 15 μl. In some cases the sample chamber has a capacity of at most 20 μl. In some cases the sample chamber has a capacity of at most 25 μl. In some cases the sample chamber has a capacity of at least 50 μl. In some cases the sample chamber has a capacity of at most 75 μl. In some cases the sample chamber has a capacity of at most 100 μl. In some cases, the size of the mixing chamber is proportional to the amount of sample and buffer to be mixed. In some cases, the capacity of the sample chamber is greater than 1 nl, 10 nl, 50 nl, 100 nl, 1 μl, 5 μl, 10 μl, 50 μl, 100 μl, 200 μl, 300 μl, 400 μl, 500 μl 600 μl 750 μl, 1 ml, or 10 ml. In some cases, the capacity of the sample chamber is less than 1 nl, 10 nl, 50 nl, 100 nl, 1 µl, 5 µl, 10 µl, 50 µl, 100 µl, 200 µl, 300 µl, 400 µl, 500 µl 600 µl 750 µl, 1 ml, or 10 ml.

Each chamber may have an input port for loading sample and chemicals for lysis and output port for drawing the lysate out. An input port or an output port maybe an automatic port that opens and closes automatically. An input port or an output port maybe opened or closed manually. An input port or an output port may contain a locking mechanism. In some cases, an input port or an output port may contain a self-locking mechanism.

In some cases, each chamber may be separated from another chamber by at least about 1 cm. In some cases, each chamber maybe separated from another chamber by at least about 2 cm. In some cases, each chamber maybe separated from another chamber by about 0.5 cm. In some cases, each chamber maybe separated from another chamber by about 10 mm. In some cases, each chamber maybe separated from another chamber by about 50 mm. In some cases, each chamber maybe separated from another chamber by about 5 mm. In some cases, each chamber maybe separated from another chamber by about 1 mm.

In some cases the microfluidic chip comprises additional chambers for purification and also for downstream processing such as conducting reactions such as PCR. The purification chamber or the PCR chamber maybe located at a fixed spacing as compared to the lysis chamber. A purification chamber or a PCR chamber maybe located about 5 cm from the lysis chamber. A purification chamber or a PCR chamber maybe located about 2 cm from the lysis chamber. A purification chamber or a PCR chamber maybe located about 3 cm from the lysis chamber.

The sample chambers may be in thermal contact with a source of thermal energy. For example, the sample chamber may be in thermal contact with a heater such as a resistive heater 160, or any other heater or thermal device known in the art, including those described elsewhere herein. As described further herein, the source of energy may heat or cool the sample chamber, including the sample within the sample chamber. In some cases, the thermal energy is applied in a cyclical fashion. In some cases, the thermal energy raises the temperature of the sample chamber. In some cases, the thermal energy causes one or more freeze-thaw cycles to occur within the sample chamber. The design of the microfluidic chip may enable the sample to undergo a temperature increase and then remain stable at the elevated temperature for a period of time (e.g., greater than 1 minute, greater than 1 hour, greater than 24 hours). This can cause thermal lysis, provide the optimum temperature for chemical or lysis or enzymatic digestion, and/or permit optimization of the lysis process. In some cases, a resistive heater 160 is coupled to a thermal transducer 170.

Often, the microfluidic chip is designed with one or more thermal insulation air grooves or apertures 150 encircling or surrounding the perimeter of the sample chamber (e.g., the device may contain more than 1, 2, 3, 4, 5, 6, 7, 8, 9, 10, 11, 12, 13, 14, 15, 20, 30, 40, 50, 75, 100, 500, 1000, or 10000 of such grooves or apertures). The air grooves may be used for thermal isolation of the sample chamber 120 from the rest of the chip during lysis, mixing, or other processes. The grooves (or apertures) may extend from the top of the chip to the bottom of the chip and enable the flow of air through the groove opening. For example, ambient air may enter the chip via a bottom opening of the groove, travel through the groove or aperture, and exit through the top opening. The one or more grooves may be positioned so that they circle or surround the sample chamber. In some cases, greater than 30%, 40%, 50%, 60%, 65%, 70%, 75%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or 99.99% of the perimeter of the sample chamber is encircled or surrounded by one or more air grooves. In some cases, less than 30%, 40%, 50%, 60%, 65%, 70%, 75%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or 99.99% of the perimeter of the sample chamber is encircled or surrounded by one or more air grooves. The insulating grooves (or apertures) are described further herein elsewhere in this disclosure.

Figure 2:
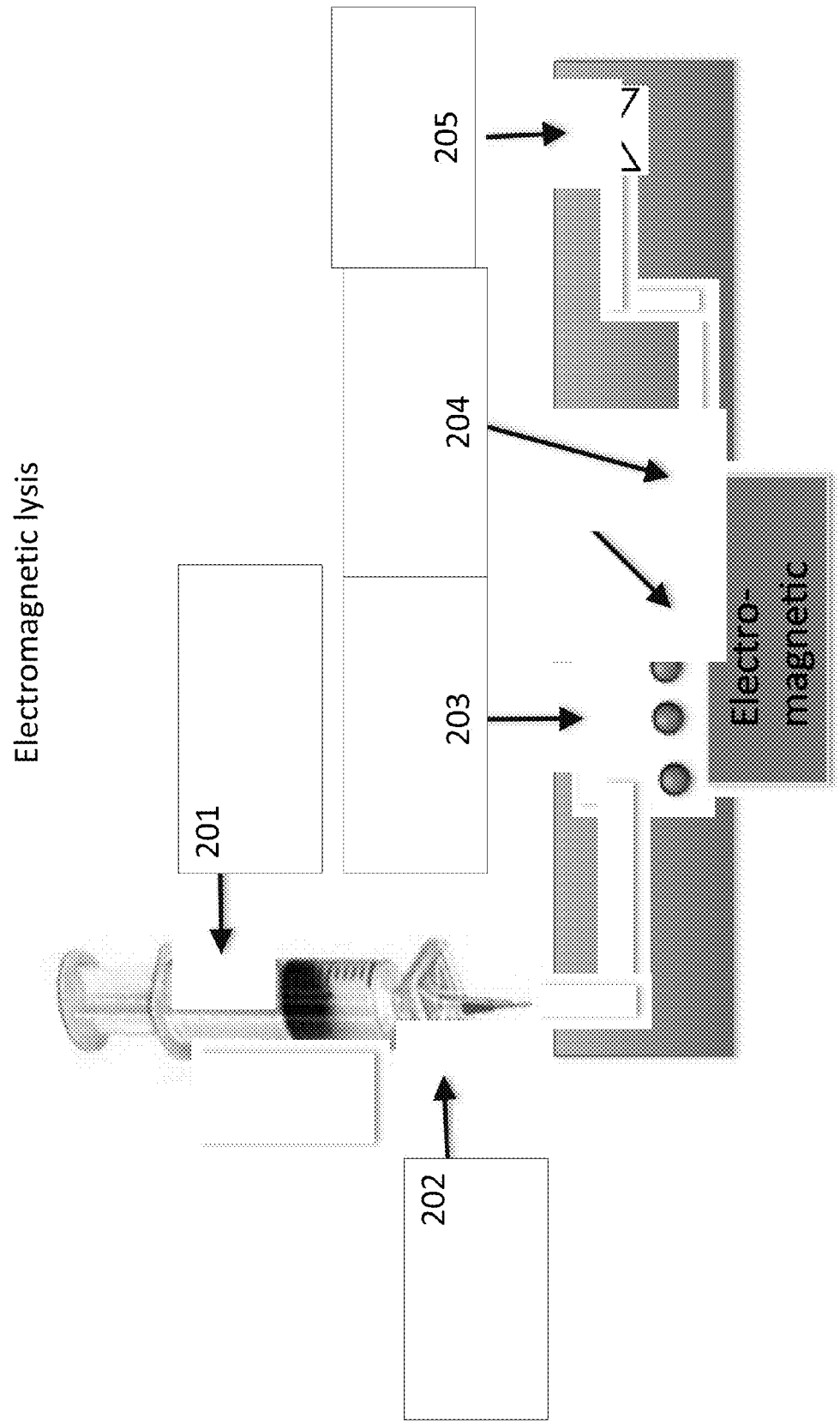
FIG. 2 is a schematic illustration of an exemplary microfluidic chip provided herein, comprising granular particles to generate friction force and collisions with structures containing nucleic acid in the sample.

Often, a sample chamber (or a plurality of sample chambers) contains one or more mechanical elements. For example, a mechanical element may be a magnetic stir bar 130 or magnetic beads (FIG. 2, 204). Mixing with a magnetically coupled stir bar 130 may enable mixing or lysis and may be incorporated for creating a well-mixed lysis environment. The stir-bar 130 and rotating magnetic field may be used to cause mechanical lysis either by the stir bar acting on particles (e.g., viral particles), nucleic-acid-containing structures (e.g., cells), magnetic particles (see FIG. 2) or any combination thereof.

The microfluidic chip may also contain a vent 180 for releasing air or fluids from the chamber 120. The microfluidic chip may be used with a source of positive or negative pressure such as syringe 110 or other type of pump. A device containing the microfluidic chip may also contain a magnet 191 and/or a motor 192.

In some cases, a plurality of chambers may be used for the lysis and/or mixing of a sample. The sample and reagents (e.g., lysis reagents) may be mixed by shuttling back and forth between two or more chambers. In some cases, mixing and temperature homogenization of the sample may occur via pressure driven flow back and forth between two or more chambers. In some cases, the back-and-forth flow may occur in tandem with chemical or mechanical lysis of the sample. In some cases, a sample is passed through filters designed to mechanically lyse the sample (see FIG. 3, 304). A microfluidic chip may be assembled via converted-tape technology and may contain a series of layers 140. For example, the sample lysis/mixing chamber 120 may be designed to fit a resistive heater 160 of a specific size (e.g., about 0.5 sq inch, 1.0 sq in., 1.5 sq in., etc.) using a converted tape technology and a set of techniques known in the art to cut channels, chambers and functional units into strips of tape. The individual strips may be laminated together to form a compact device.

Thermal Lysis

In some cases, provided herein are microfluidic chip devices capable of thermal lysis of a sample or analyte comprising nucleic-acid-containing structures (e.g., cells, microbes, viruses, bacteria, particles, etc.). The devices may be capable of raising the temperature of a sample to a particular temperature. The temperature may be a temperature that causes cellular membranes, or other nucleic-acid-containing structures, to rupture and release their contents (e.g., DNA, RNA, genomic DNA, mRNA, tRNA, miRNA, plasmid DNA, etc.). In some cases, the temperature is high enough to denature proteins that may be in the sample. Often, the cellular membranes are ruptured and/or the proteins within the sample are denatured, but the nucleic acids (e.g., DNA, RNA, etc.) within the sample remain substantially intact. An advantage of thermal lysis is that a short exposure at high temperature (greater than 70 C, greater than 75 C, greater than 80 C, etc.) may be sufficient to cause significant damage to the nucleic-acid-containing membranes (e.g., cellular membrane, organelle membrane) without significantly damaging the nucleic acids. Prolonged heating or very elevated temperatures, however, may cause irreversible denaturation of DNA. Therefore, the devices provided herein may also be designed to prevent overheating or prolonged heating.

Thermally lysed samples may contain protein and other contaminants (cell debris, envelope proteins, etc.). In some cases, some of the contaminants are removed prior to or as part of downstream analysis. For example, the contaminants may be removed in a purification chamber within the microfluidic device, or by flowing the sample through a filter within the device. In some cases, a majority of the contaminants are removed prior to downstream analysis. In some cases, the contaminants are substantially removed prior to downstream analysis.

In some cases, the microfluidic chip comprises a tube which may be wrapped around a thermal element or device. In some cases the tube is a capillary tube. In some cases, a lysis reagent and a sample are simultaneously introduced into the tube. In some cases, the tube may comprise one or more lysis reagents prior to the introduction of the sample. The tube may have one or more corrugated ridges on its inner surface. Some corrugated ridges may contain alternating small and large patterns. The corrugated ridges may perturb laminar flow of fluids in the tube. The tube maybe of a length sufficient to ensure turbulent flow of fluids.

In some cases positive and negative pressure are alternately applied on the tube in order to promote mixing of the sample with the reagent. In some cases pressure may be applied alternatively for one, two, three, four, five, six, seven, eight, nine, or ten cycles.

In some cases the tube is spirally wrapped around the heating element. In some cases only one turn of the tube is wrapped around the heating element. In some cases two, three, four, five, or six turns of the tube are wrapped around the heater. In some cases the tube is jacketed by an outer tube. In some cases the outer tube has a gas or fluid to cool down the sample after heating. The gas or fluid may flow in the opposite direction as compared to the sample. In some case, the gas or fluid may comprise air, nitrogen or water. In some cases, the capillary tube may be fluidly connected to one or more input tubes or channels at a junction.

The one or more input tubes (e.g., 1, 2, 3, 4, 5, 6, 7, or more input tubes) may connect the tube to the one or more chambers situated upstream of the tube. In some cases, the tube may be connected to a first input tube and a second input tube at a junction. In some cases the sample is introduced through the first input tube, and lysis reagent maybe through the second input tube. The ratio of the volume of the second input tube to the volume of the first input tube maybe at least 2:1. In some cases, the ratio of the volume of an input tube or channel compared to the volume of a second input tube or channel is about 1:1, 2:1, 3:1, 3:2, 4:1, 5:2, 5:3, 5:1, 4:3, 5:4, 6:1, 6:5, 7:1, or 10:1. In some cases, the ratio of the length of an input tube or channel compared to the length of a second input tube or channel is about 1:1, 2:1, 3:1, 3:2, 4:1, 5:2, 5:3, 5:1, 4:3, 5:4, 6:1, 6:5, 7:1, or 10:1. In some cases, the ratio of the pressure of an input tube or channel compared to the pressure of a second input tube or channel is about 1:1, 2:1, 3:1, 3:2, 4:1, 5:2, 5:3, 5:1, 4:3, 5:4, 6:1, 6:5, 7:1, or 10:1. In some cases, the ratio of the tube (or channel) lengths is 1:1 and the ratio of the tube (or channel) depths is 1:3; in some cases, the ratio of the tube (or channel) lengths is 1:4 and the ratio of the tube (or channel) depths is 1:1. In some cases, the ratio of the tube (or channel) lengths is 1:4 and the ratio of the tube (or channel) depths is 1:1.

In some more specific cases, a first input channel or tube may have the following dimensions and pressure: about 1.0 cm (length), about 50 um (width), about 50 um (depth), and about 0.16 Psi; and a second input channel or tube may have the following dimensions and pressure: about 1.0 cm (length), about 50 um (width), about 150 um (depth), and about 0.03 Psi. In some more specific cases, a first input channel or tube may have the following dimensions and pressure: about 0.5 cm (length), about 50 um (width), about 100 um (depth), and about 0.025 Psi; and a second input channel or tube may have the following dimensions and pressure: about 1.0 cm (length), about 50 um (width), about 100 um (depth), and about 0.05 Psi.

In some cases, the chambers fluidly connected to the tubing may be one or more sample chambers. In some cases, the chambers contain reagents. In some cases, one chamber is a sample chamber, and a second chamber contains reagents. In some cases, a plurality of chambers comprises reagents. For example, the device may contain 1 sample chamber (or more) and two chambers containing reagents for lysis or for some other sample preparation, such as immunoprecipitation reagents or PCR reagents.

The one or more input channels or tubes may be arranged in a variety of configurations. In some cases, the two input tubes or channels and the tube are arranged to form a "T". In some cases, the two input tubes (or channels) and the tube are arranged to form a "Y". In some cases, at least one input channel or tube is located at about a 10, 20, 30, 40, 50, 60, 70, 80, 90, 100, 110, 120, 130, 150, 160, 170 degree angle relative to the tube. In some cases, at least one input channel or tube is located at an acute angle relative to the tube. In some cases, at least one input channel or tube is located at an obtuse angle relative to the tube.

Heaters/Coolers:

A microfluidic chip described herein can include a thermal element which may be a heater that supplies the heat for thermal lysis. In some cases, the chip includes a cooling mechanism to cool the chamber after heating or to facilitate freeze-thaw cycles. In some aspects, the heater also functions as a cooler. In some cases, the thermal element is a thermalelectric cooler.

In some cases, the heat for thermal lysis is supplied from a resistive heater with a thermal transducer for temperature control and monitoring as shown in FIGS. 1, 3, 4, 8 & 9 among others. A microfluidic chip described herein can include a heater that is capable of heating a sample to varied temperatures at varied rates. Non-limiting examples of such heaters include resistive heater, radiative heater (e.g., infrared heater), or convective heater. Resistive heaters generally operate on the principles of Joule heating, wherein heat is generated by passing electrical current through a resistive material. Non-limiting examples of such resistive materials include resistive inks, nicrome (a composition of 80% nickel and 20% chromium), thin-film nicrome (e.g., TICER™), kanthal (a composition of iron, chromium, and aluminum), nickel-phosphorous (e.g., OhmegaPly®), cupronickel (a composition of copper and nickel), molybdenum disilicide, molybdenum discilicide doped with aluminum and/or silicon, chromium, iridium, rhodium, ruthenium, osmium, molybdenum, tungsten, copper, magnesium oxide, alumina, platinum, silicon carbide, Positive Temperature Coefficient (PTC), ceramic, barium titanate, lead titanate, bismuth telluride, antimony telluraide, bismuth chalcogenides, lead telluride inorganic clathrates, magnesium compounds, silicides, skutterudite thermoelectrics, oxide thermoelectrics, half Heusler alloys, electrically conducting organic materials, silicon-germanium, functionally graded materials, nanomaterials (e.g., quantum dots, graphene), or composites thereof, or combinations thereof. One example of a heater is a thermoelectric device, which may operate through the thermoelectric effect to establish a temperature gradient. Another example of a heater is a Peltier device, which may operate through the thermoelectric effect or Joule heating to establish a temperature gradient.

A resistive heater may be arranged as a thin-film resistive heater. In general, thin-film technology involves the shaping of one or more resistive materials into a thin layer, referred to herein as a thin-film resistive heating element, that may range from less than a nanometer to 5 mm in thickness. Advantages of thin-film technology that may be beneficial to energy transfer include higher surface area-to-volume ratios, lower thermal masses, shorter thermal paths, and more rapid thermal responses. Each of these characteristics may improve the efficiency of heat transfer from the heater to its surrounding environment and may also result in more efficient cooling of a heater and, therefore, any sample holder or sample in thermal contact with it.

Materials used for producing a resistive heater, including nickel-phosphorous and thin-film nicrome, may be particularly useful in constructing a thin-film heater. In some examples, a thin-film resistive heating element may be mounted and positioned on a carrier. A carrier may provide a substrate for the deposition of materials to form the thin-film resistive heating element and/or provide support for the thin-film resistive heating element and any associated electronic connections. Non-limiting examples of materials that may be used to construct a carrier include polyester, polyimide (e.g., Kapton), polyethylene napthalate, polyetherimide, fluoropolymers, polycarbonate, acrylic, FR-4, pre-preg (pre-impregnated) composite fibers, conformal coatings, paralyne, spin on coatings, vapor deposited coatings, coated metals, silicon-rubber, and combinations thereof. A carrier, for example, may be a flexible circuit board or a printed circuit board. Moreover, a carrier may comprise a single material or may comprise a combination of materials.

A carrier on which a thin-film heating element is mounted may also be thin in order to promote efficient heat transfer. In some examples, the thickness of a carrier is from about 0.0005 in. to about 0.2 in. In some examples, the thickness of a carrier is from about 0.0005 in. to about 0.05 in. In some examples, the thickness of a carrier is from about 0.0005 in. to about 0.03 in. In some examples, the thickness of a carrier is from about 0.0026 in. to about 0.026 in. In some examples, the thickness of a carrier is within about 0.0005 in. to 0.2 in. In some examples, the thickness of a carrier is about 0.02 in. In some examples, the thickness of a carrier is about 0.2 in.

A thin-film resistive heater may be optimized for heat transfer, such that the surface area of its heating element is larger than the surface area of a chamber in thermal contact with the heating element.

A heater may also be coated and/or covered, in whole or part, with a protective layer in order to prevent damage to the heater from, for example, mechanical contacts it makes (for example, with a sample, sample holder, and/or any other materials in mechanical contact with the heater) with various components of a device. A protective layer may or may not be designed to promote heat transfer.

The thickness of a heater may vary depending on the particular heater used and the thickness of the heater components (e.g., thin-film resistive heating element, carrier, protective layer, or any other heater component described herein). For example, the thickness of a heater may be from about 0.0001 in. to about 0.01 in. In some examples, the thickness of a heater may be from about 0.0001 in. to about 0.005 in. In some examples, the thickness of a heater may be from about 0.0001 in. to about 0.001 in. In still other examples, the thickness of a heater may be about 0.0001, 0.0005, 0.001, 0.0015, 0.0020, 0.0025, 0.0030, 0.0035, 0.0040, 0.0045, 0.0050, 0.0055, 0.0060, 0.0065, 0.0070, 0.0075, 0.0080, 0.0085, 0.0090, 0.0095, 0.01, or 0.1 in.

In some examples, the thickness of a heater may be at most about 0.1 in. In other examples, the thickness of a heater may be at most about 0.01 in. In other examples, the thickness of a heater may be at most about 0.005 in. In still other examples, the thickness of a heater may be at most about 0.0001, 0.0005, 0.001, 0.0015, 0.0020, 0.0025, 0.0030, 0.0035, 0.0040, 0.0045, 0.0050, 0.0055, 0.0060, 0.0065, 0.0070, 0.0075, 0.0080, 0.0085, 0.0090, 0.0095, 0.01, or 0.1 in.

One or more heaters used in a device of the disclosure may be arranged in variety of different configurations with respect to a chamber(s) or cartridge comprising one or more chambers. In some examples, a chamber or cartridge comprising a chamber may be in thermal contact with a heater in one direction or may be in thermal contact with a heater in multiple directions.

A heater may be in communication with a control assembly. Such control may be necessary in order to modulate the heating and/or cooling rates of a sample during thermal lysis. A device may be configured or otherwise capable of varied methods of control. In cases where a resistive heater is used, for example, the heater may be controlled by altering the electrical current that is supplied to the heater.

Microfluidic chips may have a thermal conductor to improve thermal efficiency. Thermal efficiency can be insured by isolating the chamber(s) via an air gap or groove between the chamber and the rest of the chip, as described herein. The low thermal conductivity of air insulates the chamber and captures the majority of the thermal flux (produced by the heating or cooling element) in the lysis chamber. In some cases, at least one chamber being heated is surrounded by one or more thermally insulative grooves.

In some cases, the heaters (e.g., resistive heaters) are connected to a sample chamber with an adhesive. Often, the adhesive enables optimal thermal contact between the sample chamber and the heater. In some cases, the adhesive is pressure sensitive and/or heat conductive.

Thermally Insulative Grooves (or Apertures):

In some cases, the microfluidic chip may contain apertures or thermally insulative grooves positioned around at least one chamber being heated. In some cases, the apertures or insulative grooves use air for transferring heat from the chamber. The ambient or cool air may enter the groove from the bottom, may exchange heat with the chamber, and may leave or exit the chip from the top of the groove or aperture, often with an increased temperature.

In some cases, one aperture or insulative groove is positioned around the sample chamber so that substantially all of the sample chamber is surrounded by the groove or aperture. In some cases, greater than 30%, 40%, 50%, 60%, 65%, 70%, 75%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or 99.99% of the sample chamber (or its perimeter) is surrounded by the groove.

In some cases, a plurality of apertures or insulative grooves are placed on at least one side of a chamber being heated. A plurality of apertures or insulative grooves maybe placed on multiple sides of the chamber, such as 1, 2, 3, 4, 5, or 6 or more sides of the chamber. In some instances, apertures or insulative grooves are provided on at least one side of a chamber and an air gap is provided on another side of the chamber. In some cases an air aperture, groove, or gap is provided on all sides of the chamber. In some cases, one row of apertures or grooves is placed around a sample chamber. In some cases, two parallel rows of grooves or apertures are placed around a sample chamber, e.g., more than 2, 3, 4, 5, or 6 parallel rows.

The apertures or air grooves may be any of a number of shapes. For example, a cross section of the apertures or air groove may be: circular, oval, elliptical, rectangular, rectangular with rounded edges, square, dot, triangular, trapezoidal, semi-circular, crescent, or other shape. The three-dimensional shape of the apertures or air groove may be cylindrical, cone-shaped, cubic, rectangular cuboid, pyramidal, half-domed, or other shape.

In some cases, the shape of the groove is designed to fit with the shape of the sample chamber. For example, the aperture or groove may be rectangular or oval shaped, and the edges of the aperture or groove may line up with the straight edge of a rectangular or square sample chamber. In some cases, the apertures or grooves may be curved or crescent-shaped and may be positioned so as to encircle a circular sample chamber.

The width of the aperture or air groove may be greater than about 0.001 um, 0.002 um, 0.003 um, 0.005 um, 0.01 um, 0.05 um, 0.1 um, 0.2 um, 0.3 um, 0.4 um, 0.5 um, 0.6 um, 0.7 um, 0.8 um, 0.9 um, 1.0 um, 1.1 um, 1.2 um, 1.3 um, 1.4 um, 1.5 um, 1.6 um, 1.7 um, 1.8 um, 1.9 um, 2.0 um, 3, 4, 5, 6, 7, 8, 9, 10, 20, or 30 um, or more. In some cases, the width of the air groove may be less than about 0.001 um, 0.002 um, 0.003 um, 0.005 um, 0.01 um, 0.05 um, 0.1 um, 0.2 um, 0.3 um, 0.4 um, 0.5 um, 0.6 um, 0.7 um, 0.8 um, 0.9 um, 1.0 um, 1.1 um, 1.2 um, 1.3 um, 1.4 um, 1.5 um, 1.6 um, 1.7 um, 1.8 um, 1.9 um, 2.0 um, 3, 4, 5, 6, 7, 8, 9, 10, 20, or 30 um, or more. The length of the air groove may be greater than about 0.001 um, 0.002 um, 0.003 um, 0.005 um, 0.01 um, 0.05 um, 0.1 um, 0.2 um, 0.3 um, 0.4 um, 0.5 um, 0.6 um, 0.7 um, 0.8 um, 0.9 um, 1.0 um, 1.1 um, 1.2 um, 1.3 um, 1.4 um, 1.5 um, 1.6 um, 1.7 um, 1.8 um, 1.9 um, 2.0 um, 3, 4, 5, 6, 7, 8, 9, 10, 20, or 30 um, 40 um, 50 um, 60 um, 70 um, 80 um, 90 um, 100 um, or more. In some cases, the length of the air groove may be less than about 0.001 um, 0.002 um, 0.003 um, 0.005 um, 0.01 um, 0.05 um, 0.1 um, 0.2 um, 0.3 um, 0.4 um, 0.5 um, 0.6 um, 0.7 um, 0.8 um, 0.9 um, 1.0 um, 1.1 um, 1.2 um, 1.3 um, 1.4 um, 1.5 um, 1.6 um, 1.7 um, 1.8 um, 1.9 um, 2.0 um, 3, 4, 5, 6, 7, 8, 9, 10, 20, or 30 um, 40 um, 50 um, 60 um, 70 um, 80 um, 90 um, 100 um, or more. In some cases each insulative groove is less than about 10 μm in diameter. Some insulative grooves are less than about 5 μm in diameter. Some apertures or insulative grooves are less than about 2 μm in diameter. Some apertures are less than about 3 μm in diameter. Some insulative grooves are greater than about 1 μm in diameter.

In some cases, the apertures or air grooves have different lengths. For example, the ratio of lengths of two air grooves within a device of this disclosure may be about 1:2, 1:3, 1:4, 1:5, 1:6, or other ratio.

In some cases, the apertures or grooves contain (or are filled with) an insulating material, e.g., solid material, wool, felt (e.g., with a conductivity of about 0.07 W/m·K), urethane foam (e.g., with a conductivity of about 0.021 W/m·K), silicon dioxide, or fiberglass (e.g., with a conductivity of about 0.04 W/m·K). In some cases, the material may be a fluid or liquid (e.g., water) or a gas with a low thermal conductivity (e.g., argon, nitrogen, dichlorodifluoromethane, xenon). In some cases, the insulative grooves are filed with an insulating material with a conductivity lesser than 0.15 W/m·K, less than 0.10 W/m·K, less than 0.075 W/m·K, or less than 0.05 W/m·K, less than 0.04 W/m·K, less than 0.03 W/m·K, less than 0.02 W/m·K, or less than 0.01 W/m·K. In some cases, the insulative grooves have cooled air, at least one coolant gas or a coolant fluid pumped through them. In some cases, the apertures or grooves are vacuum sealed. The vacuum maybe partial or complete.

In some cases, the one or more apertures or air grooves are arranged to surround one chamber. In some cases, the one or more apertures or air grooves are arranged to surround more than one chamber (for example, multiple sample chambers, multiple lysis chambers, multiple mixing chambers, a sample chamber and a lysis chamber, a lysis chamber and a mixing chamber, etc.). In some specific cases, the apertures or air grooves are arranged to encircle two or more lysis chambers. In some cases a larger density of apertures or insulative grooves is present on a side of the chamber closest to other chambers.

In some cases the apertures or insulative grooves prevent a majority of heat from dissipating to other chambers. The apertures or insulative grooves may be arranged such that they allow less than 80%, 70%, 60%, 55%, 50%, 45%, 40%, 35%, 30%, 25%, 20%, 15%, 10%, 9%, 8%, 7%, 6%, 5%, 4%, 3%, 2%, or 1% of heat within the sample chamber to dissipate to other chambers. The insulative grooves may be arranged such that they allow about 40% of heat to dissipate to other chambers. The insulative grooves may be arranged such that they allow about 30% of heat to dissipate to other chambers. The apertures or insulative grooves may be arranged such that they allow about 20% of heat to dissipate to other chambers. The apertures or insulative grooves may be arranged such that they allow about 15% of heat to dissipate to other chambers. The apertures or insulative grooves may be arranged such that they allow about 10% of heat to dissipate to other chambers. The apertures or insulative grooves may be arranged such that they allow about 5% of heat to dissipate to other chambers.

The apertures or insulative grooves may minimize heat loss from the heated chamber. For instance, the apertures or insulative grooves may reduce heat loss or increase efficiency by over 10%. The apertures or insulative grooves may cause a reduction in heat loss by at least about 15%, 20%, 25%, 30%, 35%, 40%, 45%, 50%, 60%, 70%, 75%, 80%, 85%, 90% or 95% as compared to a microfluidic device not comprising insulative grooves. The aperture may result in greater than 50% of the thermal energy within the chamber to be contained therein. Apertures may result in 40%, 50%, 60%, 70%, 75%, 80%, 85% or 90% of the thermal energy within the chamber to be contained therein.

The apertures or insulative grooves may improve efficiency of the lysis reaction by at least about 2%, 5%, 10%, 15%, 20%, 25%, 30%, 35%, 40%, 45%, 50%, 60%, 70%, 75%, 80%, 85%, 90% or 95% as compared to a microfluidic device not comprising insulative grooves. The efficiency of the lysis reaction maybe calculated based on a comparison of the amount of lysis product obtained, or a comparison of the total energy usage. The apertures or insulative grooves may also improve efficiency of the chip by reduced power consumption as compared to microfluidic chips not containing an aperture. The apertures or insulative grooves may reduce power consumption of the chip by about 1%. The apertures or insulative grooves may reduce power consumption of the chip by about 2%. The apertures or insulative grooves may reduce power consumption of the chip by about 4%. The apertures or insulative grooves may reduce power consumption of the chip by about 5%. The apertures or insulative grooves may reduce power consumption of the chip by about 10%. The apertures or insulative grooves may reduce power consumption of the chip by about 15%. The apertures or insulative grooves may reduce power consumption of the chip by about 20%.

Provided herein are microfluidic chips with one or more depressions configured to thermally insulate a sample chamber or lysis chamber. In some cases, the depression extends through less than 30%, 40%, 50%, 60%, 70%, 75%, 80%, 85%, 90%, 95%, or 99% of the chip (e.g., percentage of the total distance from the top of the chip to the bottom of the chip). In some cases, the depression extends through greater than 30%, 40%, 50%, 60%, 70%, 75%, 80%, 85%, 90%, 95%, or 99% of the chip. The one or more depressions may be situated so as to surround the perimeter of a sample chamber or lysis chamber.

In some cases apertures or insulative grooves are provided around a PCR chamber. In some cases apertures or insulative grooves are also provided around a purification chamber.

In some cases a further device is provided to effect the flow of a cooling gas or ambient air through the insulative grooves. Devices that may be used to effect the flow of a cooling gas include a compressor or a fan (e.g., a direct current (DC), an alternating current (AC) fan, a squirrel cage fan).

Temperature Sensors

A microfluidic chip of the disclosure may include one or more temperature sensors. Such sensors may be useful in monitoring the temperature of a sample and/or any device component. In some examples, a temperature sensor may be included in a lysis chamber, wherein the temperature sensor is immersed, in whole part, in a contained sample. In other examples, a temperature sensor may be appended to another component (e.g., a heater) in thermal contact with the sample such that it measures the temperature of the component. The component temperature may, via calibration, be used to indirectly measure sample temperature. A temperature sensor used to measure the temperature of a sample and a temperature sensor used to measure the temperature of a heater may be used in combination, or a device may include one or the other. A temperature sensor may, for example, be used to record the temperature of a component and arranged to communicate with a control device that may alter the output of a heater and/or source of cooling gas or liquid such that the desired or otherwise predetermined temperatures and/or heating/cooling profiles of thermal cycling may achieved, in some cases in the desired or otherwise predetermined order. A temperature sensor may be, for example, a thermocouple, an infrared (IR) detector, a platinum resistive temperature detector (PRTD), a resistive temperature detector (RTD). The temperature of a sample may also be measured via liquid crystals that are included in a sample holder or via infrared measurements, which do not generally require a temperature sensor in contact with the sample.

Power Sources

A microfluidic chip device of the disclosure may be powered by a power supply. The device may be electrically coupled to the power supply. As an alternative, the device may include a power supply, such as an integral power supply or removable power supply. A power supply may provide a source of electrical power to a heater of the device, source of cooling gas or liquid, and/or any other component of the device. Non-limiting examples or power supplies that may be utilized in a device of the disclosure include a solid state energy storage device (e.g., ultracapacitor), electrochemical energy storage device (e.g., lithium ion battery, NiCd battery), a battery, solar panel, a plug-in power supply, or a variable voltage power-supply. A power supply may be in communication with a control assembly in order to modulate any device to which it supplies electrical current.

Freeze/Thaw

The freeze/thaw method is commonly used to lyse bacterial and mammalian cells and other nucleic-acid-containing structures. The technique involves freezing a nucleic acid containing suspension and then thawing the material. This method of lysis causes nucleic-acid-containing structures to swell and ultimately break as ice crystals form during the freezing process and then de-crystallize during thawing. Multiple cycles are typically necessary for efficient lysis. Freeze/thaw lysis can be accomplished in a microfluidic chip described herein via the use of a thermal control circuit and heating cooling device such as a peltier. In this case subambient temperatures may be reached. The chamber may contain a sealing mechanism to minimize condensation. Additionally volume expansion of water may occur in the chamber. The chamber may have spare room or accordion like features which can allow it to grow with the ice.

Operating Performance for Thermal Lysis

Thermal Lysis Times

Microfluidic chips of the disclosure are generally capable of completing a single thermal lysis operation in a short period of time, which depends on the particular device and/or conditions employed. In some examples, a microfluidic chip of the disclosure may be capable of completing a thermal lysis operation in about 0.01 seconds ("s") to 1000 s. In some examples, a microfluidic chip of the disclosure may be capable of completing a thermal lysis operation in about 0.01 s to 500 s. In some examples, a microfluidic chip of the disclosure may be capable of completing a thermal lysis operation in about 0.01 s to 300 s. In some examples, a microfluidic chip of the disclosure may be capable of completing a thermal lysis operation in about 30 s to 300 s. In some examples, a microfluidic chip of the disclosure may be capable of completing a thermal lysis operation in about 60 s to 600 s. In some examples, a microfluidic chip of the disclosure may be capable of completing a thermal lysis operation in about 10 s to 1000 s. In some examples, a microfluidic chip of the disclosure may be capable of completing a thermal lysis operation in about 120 s to 500 s. In some examples, a microfluidic chip of the disclosure may be capable of completing a thermal lysis operation in about 20 s, 30 s, 40 s, 50 s, 60 s, 70 s 80 s, 90 s, 100 s, or 120 s. In some examples, a microfluidic chip of the disclosure may be capable of completing a thermal lysis operation in less than about 5 s, 10 s, 20 s, 30 s, 40 s, 50 s, 60 s, 70 s 80 s, 90 s, 100 s, or 120 s. In some situations, a given temperature is maintained with the aid of both heating and cooling.

Temperatures

In some examples, a microfluidic chip of the disclosure is capable of heating and/or cooling a sample to any temperature in the range of about 0° C. to 120° C. In some examples, a microfluidic chip of the disclosure is capable of heating and/or cooling a sample to a temperature in the range of about 50° C. to 100° C. In some examples, a microfluidic chip of the disclosure is capable of heating and/or cooling a sample to a temperature in the range of about 60° C. to 95° C. In some examples, a microfluidic chip of the disclosure is capable of heating and/or cooling a sample to a temperature of about 0° C., 4° C., 10° C., 20° C., 25° C., 30° C., 35° C., 40° C., 45° C., 50° C., 55° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C., 90° C., 91° C., 92° C., 93° C., 94° C., 95° C., 96° C., 97° C., 98° C., 99° C., 100° C., 101° C., 102° C., 103° C., 104° C., 105° C., 110° C., 115° C., or 120° C., or more.

A control assembly may be capable of controlling the temperature of a sample at a point during a thermal cycle, such that the temperature of the sample at that point varies minimally between replicate thermal cycles.

Generally speaking, microfluidic chip component temperatures (e.g., of a chamber, a sample, a heater, or the surface of any other microfluidic chip component described herein) may need to be monitored (e.g., by a control assembly) at regular intervals in order to achieve proper thermal lysis. The frequency at which temperature is monitored may vary, depending upon the particular device. For example, the frequency at which the temperature is monitored by a control assembly is from about 0.1 Hertz ("Hz") to about 5000 Hz. In some examples, the frequency at which the temperature is monitored by a control assembly is from about 1 Hz to about 4000 Hz. In some examples, the frequency at which the temperature is monitored by a control assembly is from about 1 Hz to about 200 Hz. In still other examples, the frequency at which the temperature is monitored by a control assembly is about 0.1, 1, 10, 25, 50, 100, 125, 150, 175, 200, 250, 300, 350, 400, 450, 500, 550, 600, 650, 700, 800, 900, 1000, 1100, 1200, 1300, 1400, 1500, 2000, 2500, 2700, 3000, 4000, 5000, 6000, 7000, 8000, 9000, or 10000 Hz. In some examples, the frequency at which temperature is monitored may be at least about 0.1, 1, 10, 25, 50, 100, 125, 150, 175, 200, 250, 300, 350, 400, 450, 500, 550, 600, 650, 700, 800, 900, 1000, 1100, 1200, 1300, 1400, 1500, 2000, 2500, 2700, 3000, 4000, 5000, 6000, 7000, 8000, 9000, or 10000 Hz.

Heating Rates

Microfluidic chips of the disclosure may heat a sample at varied heating rates. Actual heating rates may vary, for example, depending upon the volume of a sample, concentration of nucleic acids to be amplified, concentration of additional reagents necessary for nucleic acid amplification, heater performance, heater power and power density, cooling gas or liquid performance (e.g., flow rate, pressure, volume, temperature), speed of heating or cooling desired, adiabatic cooling efficiency, a heat transfer coefficient between any components, a heat transfer coefficient between any component and a cooling gas or liquid, controller speed, speed of temperature sensor data acquisition, desired quality of amplification products, configuration of the components of a microfluidic chip, or combinations thereof.

In some examples, a microfluidic chip is capable of heating a sample at a rate of about 1° C./s to 100° C./s. In some examples, a microfluidic chip is capable of heating a sample at a rate of about 10° C./s to 80° C./s. In some examples, a microfluidic chip is capable of heating a sample at a rate of about 20° C./s to 60° C./s. In some examples, a microfluidic chip is capable of heating a sample at a rate of greater than about 5° C./s, 10° C./s, 15° C./s, 20° C./s, 25° C./s, 30° C./s, 35° C./s, 40° C./s, 45° C./s, 50° C./s, 55° C./s, 60° C./s, 70° C./s, 80° C./s, 90° C./s, or 100° C./s.

Heating at Same Time as Mechanical or Chemical Lysis

A microfluidic chip described herein can perform chemical, mechanical, or electrical lysis augmented by increased temperature. In certain cases, the lysis chamber has a large surface to volume ratio and/or large flat thermal transfer surface, allowing effective coupling to a resistive heater or Peltier element capable of both heating and cooling the contents of the lysis chamber. The temperature feedback system may contain a temperature detector (such as a thermocouple, thermistor or a resistive temperature device) that can be placed in the chamber in contact with or in close proximity to the liquid in the lysis chamber in order to provide temperature feedback to a control circuit which sets or cycles the temperature of late lysis solution. In this manner freeze/thaw cycles can be made to happen in a rapid and energy-efficient way. Also, temperature lysis can occur by heating the solution in the chamber. Additionally chemical, mechanical and electrical lysis is generally more effective at elevated temperature and the chamber can be independently heated while these other forms of lysis are occurring.

Mechanical Lysis

Microfluidic chips described herein maybe useful for mechanical lysis of structures containing nucleic acids. Cell, bacterial, viral and other nucleic-acid-containing structure lysis can occur when a mechanical force is used to tear or puncture the membrane to release the nucleic acids. For instance, a microfluidic chip described herein can force a nucleic-acid-containing structure through at least one filter with openings too small for the whole structure to pass through, thereby causing the structure to break and release the nucleic acid. The microfluidic chip may contain more than one filter arranged in series. In some cases one of the filters may have sharp barbs or surfaces for shearing and bursting the cell membrane. Sharp structures may be added to the sidewalls of some of the filters to penetrate and puncture the nucleic-acid-containing structures.

A high flow rate would increase the frictional forces for complete lysis. This may cause the nucleic-acid-containing structure to rupture and the contents to spill out. Nucleic-acid-containing structures can also be lysed by use of granular particles such as glass, cubic zirconium, beads, stir bars or magnetic particles to generate friction via collisions between the cells and particles in the solution (see FIGS. 2 & 10). In some cases a plurality of beads may be present in the chamber in order to maximize frictional collision with the structures. In some cases the beads are of varying dimensions. In some instances the beads may comprise glass, ceramic or steel beads. Some beads may be at least 0.1 mm in diameter. Some beads may be up to 10 mm in diameter. Some beads may be at least about 0.1 mm, 0.15 mm, 0.2 mm, 0.25 mm, 0.3 mm, 0.4 mm, 0.5 mm, 0.6 mm, 0.8 mm, 0.9 mm, 1 mm, 1.5 mm, 2 mm, 2.5 mm, 3 mm, 3.5 mm, or 4 mm in diameter. In some instances the volume of beads in the chamber is comparable to the volume of sample. In some instances the volume of beads in the chamber is higher than to the volume of sample. In some instances the volume of beads in the chamber is at least about the same as the volume of sample and buffer. In some instances the volume of beads in the chamber is less than the volume of sample and buffer.

Figure 11:
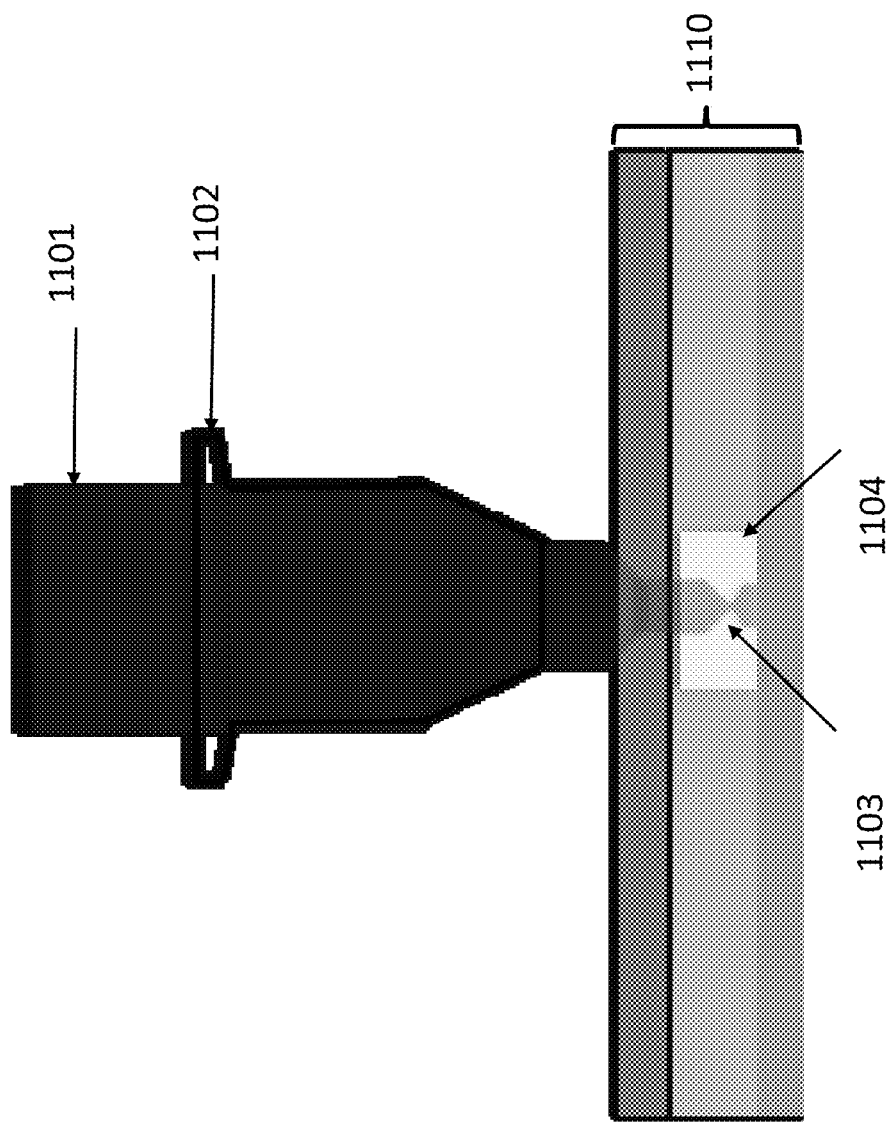
FIG. 11 is a schematic for use of focused laser beam to alter and/or to ablate cellular and tissue samples.

In some instances, ultrasonic agitation is used to create pressure waves with enough energy to disrupt and lyse the cell. Laser beams can also be used for cell lysis as shown in FIG. 11 Laser beams lyse the nucleic-acid-containing structures by ablation or by generating a shock wave and bubbles, which expand and collapse to cause lysis.

In some instances, the microfludic device comprises mixing channels that mechanically lyse the sample. In some cases the microfluidic chip comprises mixing channels that increase contact and mixing between the sample and lysis buffer or any chemical agent. Some mixing channels may result in at least 50% of the sample to come in contact with lysis buffer or any chemical agent. Some mixing channels may result in at least 60% of the sample to come in contact with lysis buffer or any chemical agent. Some mixing channels may result in at least 70% of the sample to come in contact with lysis buffer or any chemical agent. Some mixing channels may result in at least 80% of the sample to come in contact with lysis buffer or any chemical agent. Some mixing channels may result in at least 90% of the sample to come in contact with lysis buffer or any chemical agent. Some mixing channels may result in at least 95% of the sample to come in contact with lysis buffer or any chemical agent. Some mixing channels may result in at least 99% of the sample to come in contact with lysis buffer or any chemical agent. Some mixing channels may result in up to 90% of the sample to come in contact with lysis buffer or any chemical agent. Some mixing channels may result in up to 95% of the sample to come in contact with lysis buffer or any chemical agent. Some mixing channels may result in up to 100% of the sample to come in contact with lysis buffer or any chemical agent. In some cases, at least one mixing channel comprises at least one loop. Some mixing channels comprise a serpentine path from one chamber to another. In some mixing channels, the direct distance between the chambers is shorter than the path within the channel. In some mixing channels, the direct distance between the chambers is half than the path within the channel. In some mixing channels, the direct distance between the chambers is less than one third of the path within the channel. Some mixing channels may comprise patterned grooves in the walls. In some cases, the grooves comprise a staggered herringbone pattern. In some cases the grooves are v-shaped, c-shaped, u-shaped, j-shaped, i-shaped, x-shaped, l-shaped or t-shaped. In some cases, the channel has at least one aperture configured to insulate. In some cases, the grooves form a helical pattern. In some cases multiple mixing channels are arranged in series. In some cases multiple mixing channels are arranged sequentially. In some cases multiple mixing channels are arranged cuncurrently. In some microfluidic chips at least mixing channel is used for mechanical lysis while at least another is used for chemical lysis. In some cases, mixing channels have beads or objects placed in them to increase mechanical lysis.

Sample Mixing with Stir Bar

Micro-stir bar mixing utilizes a rotating bar or rotor to actuate mixing. The stir bar is typically is magnetically couple to an external motor which provides rotational force. The magnetic material of the stir bar is usually encapsulated with materials that are compatible with the reagents, chemical and biomolecules to be mixed. The encapsulating material should also withstand the conditions of the experiments such as temperature and pH. When a rotating external magnetic field is applied to the encapsulated stir bar, it is magnetize and experience a torque through interaction between its internal magnetization and the external field. When the torque exceeds the friction force, the rotor will rotate following the external magnetic field. The stir bar mixing approach offers several advantages and provides performance characteristics and advantages such as (1) Rapid mixing in a chamber which can be realized within a short time, (2) The mixers can be used in an array for effective mixing in a larger reaction chamber for sequential flow analysis, (3) Since the magnetic actuation is applied externally, it eliminates the need for connecting wires and reduces the control complexity and mechanical complexity of the microfluidic chip, and (4) The mixer can be used for a wide variety of fluids with different physical, chemical and electrochemical characteristics. The stir bar maybe made of a magnetic material compatible with the sample in the chamber. In some cases the stir bar is coated with a plastic material. In some instances, the stir bar is coated with a metallic material. In some cases, the stir bar is coated with a biocompatible or inert material. Some stir-bars may have rough surfaces to enhance mechanical lysis. Some stir-bars may have bristled surfaces to enhance mechanical lysis. Some stir bars occupy less than about 1% of the available volume in the chamber. Some stir bars occupy less than about 5% of the available volume in the chamber. Some stir bars occupy less than about 10% of the available volume in the chamber. Some stir bars occupy less than about 15% of the available volume in the chamber. Some stir bars occupy less than about 2% of the available volume in the chamber. Some stir bars occupy less than about 4% of the available volume in the chamber. Some stir bars are about 2 mm×6 mm in size. Some stir bars are about 1 mm×5 mm in size. Some stir bars are about 0.5 mm×5 mm in size. Some stir bars are about 2 mm×4 mm in size. Some stir bars are about 2 mm×5 mm in size. Some stir bars are about 0.5 mm×4 mm in size. Some stir bars are about 1 mm×4 mm in size.

Filters Between Chambers

In some microfluidic chips, channels may be fabricated through the wall between the chambers and can hold filters between the chambers or themselves act as filters. The lysis occurs when particles to be lysed are forced through these filters because the filter openings are too small for the nucleic acid containing membrane to pass through intact. Filters can also be chemically treated to lyse the samples such as with FTA paper material. The channel edges between the chambers can be fabricated with small narrow contractions or knife-edge like protrusions for bursting the nucleic acid containing membrane to spill out their nucleic acid contents. A pressure source for instance, but not limited to a syringe may be be used to generate flow rates that increase the frictional forces in the narrow contractions filter wall for complete lysis of the particle. The pressure source creates the pressure to move of the liquid back and forth between the chambers, passing the liquid through the lysine filter or features between the two chambers.

Use of at Least One Pressure Source for Positive and Negative Pressure

A microfluidic chip described herein may use a pressure source to create at least one of positive and negative pressure to actuate fluid movement. A syringe coupled to the lysis chamber and actuated by a linear actuator can create positive and negative pressure. The amount of pressure, and therefore liquid flow, created by the syringe can be controlled by a microprocessor that commands the linear actuator. The negative and positive pressure may also be applied with a plunger or linear actuator in fluid connection with the chamber. In some cases, the pressure source maybe a pump. In some cases the pressure source maybe operated by pneumatic control. Some times the pressure source maybe a non-animate source. In some cases the pressure is applied by use of an applicator. Pressure may be controlled by use of a gas. Feedback systems such as position sensors, fluid sensors and electric optical sensors can be incorporated to make the syringe movement a closed loop depending on the position of the syringe, or the movement of fluid in the licensed chamber.

The pressure source can be controlled to move the fluid according to a lysis protocol. The fluid can be forced through a lysis filter (one with small structures to break open the nucleic-acid-containing structures), debris filter or similar filters. The pressure source can also create turbulent, pulsed, or chaotic flow in the lysis chamber in order to mix the sample. The type of flow created can be controlled by the speed for instance of syringe actuation.

Chemical Lysis

Lysis chemicals may be used to break down the nucleic-acid-containing structures. A variety of chemicals and lysis protocols may be used to lyse the wide range of cell types, viral envelopes, nucleic-acid-containing structures, etc. For instance, ammonium chloride, acts on erythrocytes only and is ineffective in lysing non-erythrocytic mammalian cells. Nonionic and ionic detergents are used to disrupt the cell membranes by solubilizing membrane proteins and lipids. Non-ionic detergent such as Triton X-100, act more slowly and are primarily used in sample preparations for downstream assays requiring protein structure and function to be maintained. Ionic detergents such as Sodium dodecyl sulfate (SDS) act more quickly to totally denature proteins and can be used in sample preparations for nucleic acid, as they generally denature DNAse and RNAse enzymes.

The detergents are generally incapable of bacterial lysis since the detergents act on cell membranes. For bacterial lysis, lysozymes can be used as a pretreatment step to destroy the cell wall and for enzymatic degradation.

High concentrations of chaotropic salts such as guanidinium thiocyanate and guanidinium chloride lyse cell membranes by disrupting protein intermolecular forces. They denature RNAses as well as membrane proteins, and so are valuable in nucleic acid extraction. The high salt concentration of chaotropic salts also enables strong binding of the nucleic acids selectively onto silica surfaces.

In some cases, the amount of lysis reagent or buffer provided is proportional to the amount of sample to be lysed. In some cases, the ratio of reagent to sample maybe 1:1, 2:1, 3:1, 3:2, 4:1, 5:2, 5:3, 5:1, 4:3, 5:4, 1:2, 1:3, 1:4 or 1:5.

Chemical Lysis with Optional Multiple Chamber Mixing

Multiple chambers of the microfluidic chip may be assembled from laser cut layers and assembled using converted tape technology (converted tape technology refers to a set of techniques known in the art to cut channels, chambers and functional units into strips of tape with dies, lasers or other means in individual pieces of tape and then laminating them together to form a useful device such a design can typically be converted to an injection molding. The layers with adhesive (with for instance a silicone pressure sensitive adhesive) have the adhesive patterned (the adhesive is removed where it would otherwise contact the fluid) to prevent any interference of the adhesive with the sample or fluids. A thin wall with an open conduit can divide multiple chambers, for instance two chambers, such that fluid can be moved back and forth between the chambers for mixing during a lysis process, for instance during a chemical lysis. Each chamber may have several ports, one for loading sample and chemicals for lysis, and others dedicated to moving the sample and chemicals back and forth between the chambers for mixing and for sample output after lysis. The chemicals for lysis may be stored in one or multiple fluid pouches.

The fluid may be introduced at the appropriate time into each chamber via controlled electromechanical bursting of the fluid pouches allowing the fluid to enter the chamber via the fluid pouch's own channel or a shared input channel. The fluid pouches can be burst in a number of ways, including through the use of negative pressure exerted by the syringe, for example exerting negative pressure on a weak point of the fluid pouch or against a sharp point. In some cases, the fluid pouches may be bottles or other receptacles. The filling of the chamber with sample or lysis buffer can be accomplished by gravity or by simultaneously to, or just prior to, fluid presentation at the chamber, retracting the syringe to create suction in the chamber. The fluid can be forced into the microfluidic chip by the negative pressure created by for instance, a syringe, where the syringe creates space for air that would otherwise take up space needed by the fluid, or the fluid can enter the chamber and the air can leave via a vent (which may be properly sealed against contamination with a material such as urethane or porextm that allows air to pass but not liquid or nucleic acid, in this way the fluid filling can be separated from the syringe action. The movement of the lysis buffers and sample can be actuated by positive or negative pressure from the coupled syringe. The output port can also act as an input port to deliver the lysate/sample waste back into the chamber. The output port can also act as an input port to deliver the lysate/sample waste back into the chamber after the nucleic acids have been removed from the lysate. Heating during the chemical lysis can be effected by heating the desired chamber with a resistive heater, peltier or other heat source in thermal contact with said chamber. Temperature feedback can be provided by a thermal transducer attached in thermal contact with the sample and lysis buffers in the chamber. Around the chambers thermally insulative grooves may be provided as described above, that utilize ambient air for insulation around the chambers and to prevent thermal cross talk with the rest of the microfluidic chip.

Each chamber may have an input port for loading sample and chemicals for lysis and output port for drawing the lysate out. An input port or an output port maybe an automatic port that opens and closes automatically. An input port or an output port maybe opened or closed manually. An input port or an output port may contain a locking mechanism. In some cases, an input port or an output port may contain a self-locking mechanism. The chemicals for lysis maybe stored in one or multiple fluid receptacles such as fluid pouches. In some cases, the fluid can be provided at the appropriate time into the chamber via microcontroller controlled electromechanical bursting of fluid pouches allowing the fluid to enter the chamber via the fluid pouch's own channel or a shared input channel. In some cases the channels are of varying sizes proportional to the amount of each fluid desired in the chamber. For instance, in some cases, if the amount of one chemical agent desired is 2 times the amount of a second agent, then the input channel for said first agent has about two times the diameter of the channel for the first agent. In some cases, the size of the fluid pouch is proportional to the amount of reagent desired in the chamber. In some cases each fluid pouch carries about the amount of reagent needed in the chamber. In some cases each fluid pouch carries at most about 10% more than the amount of the reagent needed in the chamber. In some cases each fluid pouch carries at least about 1% more than the amount of the reagent needed in the chamber. The filling of the chamber with sample, reagents or lysis buffer can be accomplished by gravity or simultaneously to or just prior to, fluid presentation at the chamber, by creating suction in the chamber for instance by retracting a syringe. The movement of the lysis buffers and sample can actuated by pressure from a coupled syringe. The output port can also act as an input port to deliver the lysate/sample waste back into the chamber after the nucleic acids have been removed from the lysate.

Chemical Lysis Optionally with Magnetic Stir Bar Mixing

A magnetic stir bar may be enclosed inside at least one chamber during the assembly of the device. A separate rotational external magnet can drive a stir bar's motion through magnetic coupling from the motor to the stir bar or an assembly of electromagnets (i.e., coils) located near the lysis chamber such as that in a brushless motor actuated by appropriate electronics. In some cases, the stir bar is not a magnet, but made of a magnetic material such as iron. In case a rotating magnet is provided below the lysis chamber, the stir bar need not be made of a magnet, but simply a magnetic material. The stir bar maybe made of a magnetic material compatible with the sample in the chamber. In some cases the stir bar is coated with a plastic material. In some instances, the stir bar is coated with a metallic material. In some cases, the stir bar is coated with a biocompatible or inert material. Some stir-bars may have rough surfaces to enhance mechanical lysis. Some stir-bars may have bristled surfaces to enhance mechanical lysis. An electric motor coupled to magnetic-stirrer assembly below the chamber can be used to rotate the magnetic stir bar inside the chamber causing mixing. Heating during the chemical lysis can be effected by heating the chambers (or single chamber) with a resistive heater, peltier or other heating means. A thermal transducer can be attached in thermal contact with the sample and lysis buffers in the chamber to provide temperature feedback. Around the chambers thermally insulative grooves may be placed that utilize ambient air for insulation around the chambers and to prevent thermal cross talk with the rest of the microfluidic chip.

Overview of Devices Containing Patterned Channels

The devices provided herein may include one or more patterned mixer or lysis channels. This disclosure also provides methods that include the use of one or more patterned mixer or lysis channels.

Figure 5:
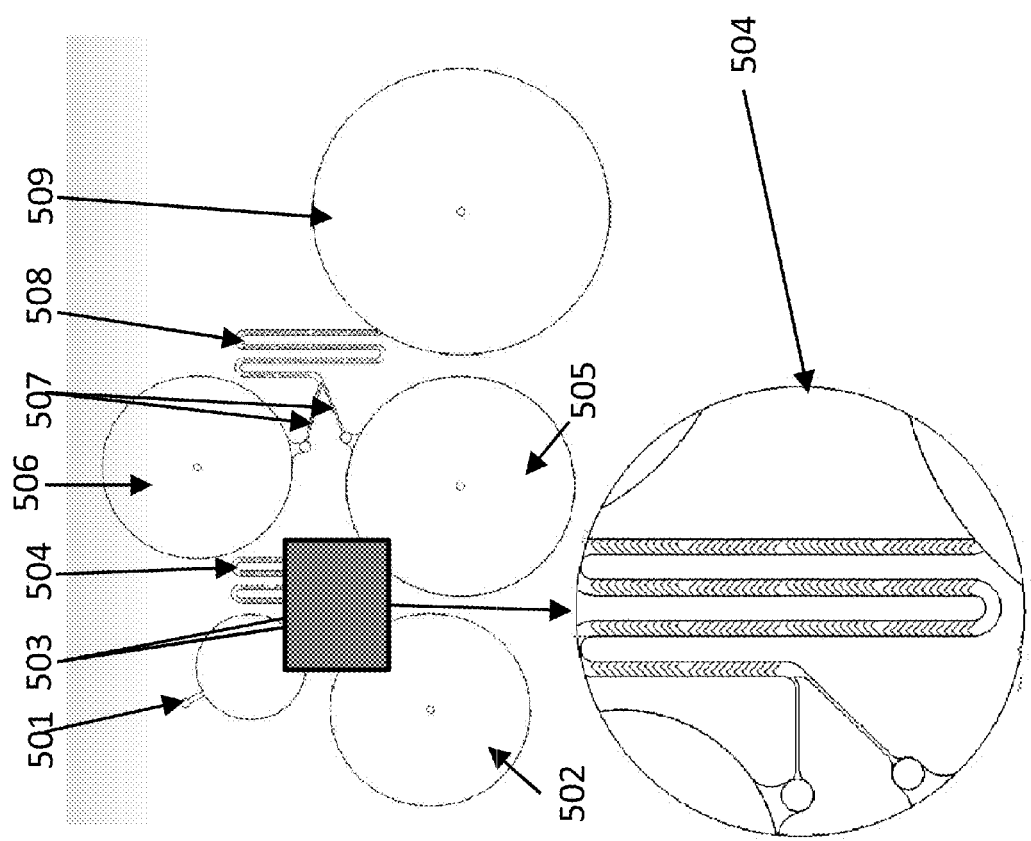
FIG. 5 is a multi-view schematic of an exemplary microfluidic chip described herein, comprising a herringbone mixer.

An exemplary patterned channel is provided in FIG. 5. The patterned channel (e.g., 504) may be connected to one or more input channels (e.g., 503). The patterned channel may also be connected to one or more chambers situated upstream of the patterned channel (e.g., 501, 502). The one or more input channels (e.g., 1, 2, 3, 4, 5, 6, 7, or more input channels) may connect the patterned channel to the one or more chambers situated upstream of the patterned channel. In some cases, the chambers may be one or more sample chambers. In some cases, the chambers contain reagents. In some cases, one chamber is a sample chamber, and a second chamber contains reagents. In some cases, a plurality of chambers comprises reagents. For example, the device may contain 1 sample chamber (or more) and two chambers containing reagents for lysis or for some other sample preparation, such as immunoprecipitation reagents or PCR reagents.

The one or more input channels may be arranged in a variety of configurations. In some cases, the two input channels and the patterned channel are arranged to form a "T". In some cases, the two input channels and the patterned channel are arranged to form a "Y". In some cases, at least one input channel is located at about a 10, 20, 30, 40, 50, 60, 70, 80, 90, 100, 110, 120, 130, 150, 160, 170 degree angle relative to a patterned channel. In some cases, at least one input channel is located at an acute angle relative to a patterned channel. In some cases, at least one input channel is located at an obtuse angle relative to a patterned channel.

In some cases, the ratio of the volume of an input channel compared to the volume of a second input channel is about 1:1, 2:1, 3:1, 3:2, 4:1, 5:2, 5:3, 5:1, 4:3, 5:4, 6:1, 6:5, 7:1, or 10:1. In some cases, the ratio of the length of an input channel compared to the length of a second input channel is about 1:1, 2:1, 3:1, 3:2, 4:1, 5:2, 5:3, 5:1, 4:3, 5:4, 6:1, 6:5, 7:1, or 10:1. In some cases, the ratio of the pressure of an input channel compared to the pressure of a second input channel is about 1:1, 2:1, 3:1, 3:2, 4:1, 5:2, 5:3, 5:1, 4:3, 5:4, 6:1, 6:5, 7:1, or 10:1. In some cases, the ratio of the channel lengths is 1:1 and the ratio of the channel depths is 1:3; in some cases, the ratio of the channel lengths is 1:4 and the ratio of the channel depths is 1:1. In some cases, the ratio of the channel lengths is 1:4 and the ratio of the channel depths is 1:1.

In some more specific cases, a first input channel may have the following dimensions and pressure: about 1.0 cm (length), about 50 um (width), about 50 um (depth), and about 0.16 Psi; and a second input channel may have the following dimensions and pressure: about 1.0 cm (length), about 50 um (width), about 150 um (depth), and about 0.03 Psi. In some more specific cases, a first input channel may have the following dimensions and pressure: about 0.5 cm (length), about 50 um (width), about 100 um (depth), and about 0.025 Psi; and a second input channel may have the following dimensions and pressure: about 1.0 cm (length), about 50 um (width), about 100 um (depth), and about 0.05 Psi.

Often, the patterned channel may be used to mix the sample, or to mix the sample with one or more reagents. In some cases, the patterned channel is used for sample lysis. In some cases, the patterned channel is heated in order to facilitate sample lysis. In some cases, the channel contains one or more mechanical elements (e.g., microbeads) in order to facilitate sample lysis. In some cases, the patterned channel contains lyophilized reagents (e.g., lysis reagents) that are configured to contact the sample upon entry of the sample into the patterned channel. The lyophilized reagents may coat the surface of the interior of the patterned channel or may be present in free form within the channel.

The patterned channel may be configured to perturb the laminar flow of a fluid flowing through the patterned channel. The patterned channel may be configured to effect turbulent flow of a fluid flowing through the patterned channel.

The patterned channel may contain grooves with one or more patterns. Often, the patterns are grooves or indentations in the interior walls. The grooves or indentations are configured to facilitate sample lysis or sample mixing. In some cases, the grooves or indentations are v-shaped (e.g., FIG. 6, 603) (in some cases, v-shaped grooves may have arms with different lengths). In some cases, the grooves or indentations are in a repeating pattern. The grooves or indentations may be other patterns as well, e.g., vertical lines, horizontal lines, diagonal lines, triangles, semi-circles, curves, single curves, double cuves, m-shaped, w-shaped, T-shaped, S-shaped, v-shaped, c-shaped, u-shaped, j-shaped, i-shaped, x-shaped, l-shaped and any other pattern or mixture of patterns. In some cases, the grooves or indentations are arranged in a staggered pattern. For example, the grooves or indentations may be arranged in a repeating pattern that shifts into a repeating pattern of the same shape in the opposite orientation. In some cases, the staggered pattern occurs after every shape, every two shapes, every three shapes, every four shapes, every five shapes, every six shapes, every seven shapes, every eight shapes, every nine shapes or every ten shapes.

The patterned channel may be arranged into a variety of shapes. Often, the patterned channel is curved. For example, the patterned channel may be C-shaped, S-shaped, or serpentine shaped (e.g., 504). In some cases, the patterned channel is arranged as a helix or spiral. In some cases, the patterned channel is straight or linear.

In some cases, the patterned channel is connected to a thermal element or device. In some cases, the thermal element is a heater. The chip may have at least one aperture configured to insulate the patterned channel. The chip may have a plurality of apertures configured to insulate the patterned channel. In some cases, the microfluidic chip has 2, 3, 4, 5, 6, 7, 8, 9, 10, 12, 14, or 15 apertures or insulative grooves to insulate the patterned channel.

In some cases, the one or more patterned channels are connected with one or more chambers (e.g., FIG. 5, 505) located downstream of the one or more patterned channels. In some cases, the one or more patterned channels are connected with one or more channels located downstream of the one or more patterned channels. In some cases, the one or more patterned channels are connected to one or more patterned channels located downstream of the one or more patterned channels. For example, a patterned channel may be directly connected to a second patterned channel that maybe located downstream of the channel. Or, in some cases, the patterned channel is connected via a second chamber or channel to the second patterned channel. In some cases, the patterned channel is connected to a channel that is not patterned. The patterned channel may be downstream or upstream of the channel that is not patterned. In some cases, a patterned channel is heated. In some cases, the heated patterned channel is surrounded by at least one insulative groove or aperture. In some cases, one or more chambers maybe in fluid contact with two or more patterned channels. The one or more chambers maybe heated. The heated chamber may have thermally insulative grooves or apertures placed around it in order to minimize transfer of heat to one or more patterned channels. In some cases, the chambers and the patterned channels are all heated. Thermally insulative grooves maybe present around the chambers and patterned channels.

In some cases, a device provided herein contains greater than 1, 2, 3, 4, 5, 6, 7, 8, 9, or patterned channels fluidly connected. In some cases, a device provided herein contains greater than 1, 2, 3, 4, 5, 6, 7, 8, 9, or 10 patterned channels arranged in parallel.

In some cases, this disclosure provides lysis methods in which a sample is lysed within a patterned channel. In some cases, the sample is mixed within a channel (that may or may not be patterned) and then travels to a second channel (e.g., a patterned channel), where is undergoes lysis. In some cases, the sample is washed in the pattern channel or the second channel. The wash buffer may be provided by a chamber fluidly connected with a patterned channel or other channel or chamber containing the sample.

In some cases the patterned channel is about 1 cm to about 15 cm in length. In some cases the patterned channel is about 1 cm, 2 cm, 2.5 cm, 3 cm, 3.5 cm, 4 cm, 4.5 cm, 5 cm, 5.5 cm, 6 cm, 6.5 cm, 7 cm, 7.5 cm, 8 cm, 8.5 cm, 9 cm, 10 cm, 11 cm, 12 cm, 13 cm, 15 cm, 17 cm, 20 cm, 25 cm, 30 cm, or 35 cm in length. A patterned channel maybe between about 30 µm to about 500 µm in width. A patterned channel maybe about 10 µm in width. A patterned channel maybe about 20 µm in width. A patterned channel maybe about 40 µm in width. A patterned channel maybe about 50 µm in width. A patterned channel maybe about 75 µm in width. A patterned channel maybe about 100 µm in width. A patterned channel maybe about 120 µm in width. A patterned channel maybe about 125 µm in width. A patterned channel maybe about 150 µm in width. A patterned channel maybe about 200 µm in width. A patterned channel maybe about 250 µm in width. A patterned channel maybe about 225 µm in width. A patterned channel maybe about 300 µm in width. A patterned channel maybe about 350 µm in width. A patterned channel maybe about 400 µm in width. A patterned channel maybe about 450 µm in width. A patterned channel maybe about 500 µm in width. A patterned channel maybe about 600 µm in width. The patterned channel maybe between about 30 µm to about 250 µm in depth. The patterned channel maybe about 40 µm in depth. The patterned channel maybe about 50 µm in depth. The patterned channel maybe about 60 µm in depth. The patterned channel maybe about 75 µm in depth. The patterned channel maybe about 80 µm in depth. The patterned channel maybe about 100 µm in depth. The patterned channel maybe about 125 µm in depth. The patterned channel maybe about 150 µm in depth. The patterned channel maybe about 175 µm, 200 µm, 210 µm, 225 µm or 250 µm in depth.

Chemical Lysis with Patterned Mixer or Channel

Chemical lysis with a patterned mixer such as a herringbone mixer may begin with the sample being inserted into a chamber (e.g., FIG. 5, 501). The herringbone mixer is simple, elegant, and easy to fabricate. It may contain a rectangular channel with herringbone grooves in one or more walls of the channel (see FIG. 5, 504 & FIG. 6). The herringbone grooves are generally v-shaped and arranged in a repeating pattern. The lysis reagent mix is released or stored in chamber (e.g., FIG. 5, 502) at the appropriate time via microcontroller control of for instance the electromechanical bursting of fluid pouches containing the reagents. Suction is applied from chamber (e.g., FIG. 5, 505). (or positive pressure exerted onto 501 and 502) to draw lysis chemicals and the sample to be lysed into chamber 505 through the channel dimensions to draw the fluid through the mixing channel (504). The fluids are mixed in the staggered herringbone-mixing channel 504. The mixed solution is transported into chamber 505 to complete lysis at room temperature or it can be heated if required with resistive heater, peltier or other thermal device attached under the chamber 505. Any additional reagents such as ethanol or isopropyl alcohol required by the lysis or downstream processes is released or stored in chamber (e.g., FIG. 5, 506) or additional chambers at the appropriate time via microcontroller control of for instance the electromechanical bursting of fluid pouches containing the reagents. Suction from a chamber 509 (or pressure exerted onto 505 and 506) transports the lysate mixture and other fluids (such as ethanol or isopropyl alcohol) from chamber 505 and chamber 506, respectively to combine and mix in the second herringbone channel and are drawn into chamber 509 or another portion of the microfluidic chip.

Electrical Lysis.

To induce cell lysis, the cells or nucleic-acid-containing structures may be exposed to electric fields. In the presence of pulsed electric fields (PEF5), membranes are destabilized and become permeable to macromolecules, nucleic acids, and cytoplasmic contents depending on the contents of the membrane. As the combination of pulse length and electric field strength reach critical values the nucleic-acid-containing structure is lysed by breakdown of the structure and nucleic acids are released. The critical electric field value (voltage) is the most important parameter for lysis by PEF, and varies between types of bacteria and mammalian cells or nucleic-acid-containing structures due to deviations in their shape and size. Alternatively, an electroporation lysis method that uses a high frequency AC sinusoidal current can also give the same effect through similar mechanisms.

Electrical Lysis with Electrode Deposition

To pattern the metal electrodes on the microfluidic chip different approaches such as physical vapor deposition of metals such as platinum or gold, electrode deposition, and deposition of conductive inks can be used. Other electrode fabrication techniques known in the art such of photolithography, thermal processing with sputtering of metals can be used to deposit electrodes in the microfluidic chip. Photolithography processes known in the art also form the microfluidic via layers and chambers layers on the selected plastics disposable material. These approaches enable precise positioning of multiple electrodes and good interfacial adhesion of the electrodes and the disposable substrate. These electrodes are capable of sustaining high electric fields without degradation during the lysis process. Platinum electrodes are preferred due to their chemical inertness with chemicals and biomolecules such as nucleic acid, proteinase K etc. although other metals will also function with the surface passivation. Different shapes of electrode such as cylindrical electrodes can be used to increase the electric field strengths or saw-tooth shapes of the micro electrodes can also be used if non-uniform electric field is required.

Other Lysis Additives/Facilitators

Samples can be treated with various agents to aid the lysis process. For instance, lysis can be promoted by suspending cells in a hypotonic buffer, which cause them to swell and burst more readily under physical shearing. Lysozyme can be used to digest the polysaccharide component of yeast and bacterial cell walls. Alternatively, the addition of glass beads can facilitate the crushing of cell walls for example the lysis of yeast cells or some bacterial pathogens (e.g., mycobacterium, etc.) Surfactants may also be used on particle membrane with lipid double-layer to solubilize the lipid membranes.

Features of Microfluidic Chips Described Herein

Fluid Pouch Reagent Storage

In some cases, reagents for use in the processes described herein (e.g., lysis, PCR, washing, etc.) are present one or more fluid pouches positioned within the microfluidic chip. In some cases, a microfluidic chip may contain at least 1, 2, 3, 4, 5, 6, 7, 10, 20, or more fluidic pouches. In some cases, the one or more fluid pouches are located on a site external from the chip. Often, the fluid pouches may be ruptured in an automated method. The microfluidic chip lysis system may contain all reagents, premeasured, ready-for-use, temperature stabilized fluid pouches but are ruptured in an automated style at the appropriate time in the lysis protocol. The fluid pouch rupture can occur by microprocessor control, via electromechanical actuators that squeeze the fluid pouches to the point of rupture. Electromechanical actuators can also pierce the fluid pouches with this sharp point, or squeeze the fluid pouches on to a sharp point, which is on the microfluidic chip. The fluid pouches can also be made with a portion of the pouch weakened (via scoring for instance) such that the fluid pouch bursts open in a controllable manner. The fluid pouch is sealed to the lysis chamber and upon bursting the fluid is drawn into the lysis chamber via the pressure created by the syringe or via pressure-actuated valve on the fluid pouch fluidic channel.

Fluid pouches are well suited to storage of flammable and volatile fluids such as isopropyl alcohol and ethanol, which can be required for lysis. They can provide a means to ship these reagents preloaded on to the cartridge. Fluid pouches are available in many styles known in the art such as Mylar™ and other polymer films. These films can be coated with a thin layer of aluminum or oxygen barrier to preserve the contents. Small plastic bottles, such as polyethylene, polypropylene and other polymers can also store many different types of liquids. These small plastic bottles may be pierced in a controlled fashion in order to integrate them with a disposable cartridge. A piercing needle can be heated, for instance by electric Joule heating, in order to facilitate piercing. Lysis protocols often require that different reagents be used at different times. For instance, lysis can begin with Chaotropic salts, and then sometime later (for instance 10 min.) and alcohol such as isopropyl alcohol or ethanol is required to be mixed with the solution to precipitating the DNA and to make it more concentrated because other contaminants in the solution are not precipitated at the same time. The microprocessor controlled, electromechanically actuated, fluid pouch bursting allows these different reagents to be stored separately and added to the lysis chamber at the appropriate times see FIG. 11. When the 1st reagent is needed, the microprocessor can command the electromechanical actuator to burst the fluid pouch and simultaneously, or just before, command these syringe to draw the fluid in the pouch into the lysis chamber. After an appropriate time past, the microprocessor can command a similar sequence of events to introduce a 2nd fluid to the lysis chamber. This process can be repeated for as many reagents are needed to be delivered to the lysis chamber separately. This technique can also be used to store reagents separately for longer shelf life. Each reagent can be stored in an individual fluid pouch and each can be introduced to the lysis chamber sequentially or concurrently. Fluid pouches are a recognized way of preserving a measured quantity of reagents for long shelf life in harsh conditions. They are available in many configurations and materials depending on the reagent to be stored in the desired shelf life.

The fluid pouch can be made of polymer monolayer foils from plastics for instance polypropylene (PP), polyethylene (PE), polystyrene (PS), polyethylene terephthalate (PET), polycarbonate (PC), cyclic olefin (co) polymers (COC/COP) and thermoset polymers like polyimide (PI). Some fluid pouches are made of polymer multilayer or compound foils where two or more different polymers are co-extruded or laminated onto each other. Some fluid pouches comprise metal foil such as aluminum. Fluid pouches may also comprise paper material such as nitrocellulose.

In some cases, one or more fluid pouches are located on the surface of the microfluidic chip. Often, the fluidic pouches are fluidly connected to one or more sample, lysis, and/or mixing chambers. Channels may connect the fluid pouches to the chambers.

Material Selection and Compatibility

To select a full set of materials to build a microfluidic chip described herein, one may consider the fabrication process used to make the microfluidic chip device. The access to these materials make it possible to design simple to complex microfluidic chip devices with specific optical characteristics, biological or chemical compatibility, faster prototyping or lower production costs, the possibility of electrosensing, among others and the final choice depends on the aimed application. Laser cut layers may be assembled using converted tape technology whereby the layers with adhesive (for instance a silicone pressure sensitive adhesive) have the adhesive patterned (the adhesive is removed where it would otherwise contact the fluid) such that the layers are laminated together to form a compact laminate device. This approach allows various materials to be used together, rapid prototyping and different materials can be incorporated in a single device such Delran, polypropylene, polycarbonate (PC), acrylic, Poly(ethylene terephthalate) (PET). The design of the microfluidic chip with this technology can be readily converted to an injection molded design. All the technologies in this document are meant to be compatible with injection molding techniques. Some assembly or secondary processes are contemplated, and in some cases sealing film may have to be applied to injection-molded pieces. Additionally mechanical connections such as with screws, gaskets, vapor/aerosol barriers, bolts or luer locks are also contemplated.

Nucleic Acid Control Stabilized in Chamber

A process control, or internal control can be temperature stabilized and stored in the lysis chamber. A number of techniques are available to store suitable process or internal controls. The design of the chamber is such that the top layer of the chamber can be left open to facilitate lyophilization or other temperature stabilization techniques. The chamber also presents a large surface area, which facilitates lyophilization or other temperature stabilization techniques. Process controls are typically nucleic acids in a stable matrix. For instance, Armored RNA sold by Asuragen packages the RNA in The coat protein of *Escherichia coli* bacteriophage MS2. This would qualify as a process control because the code proteins packaging the control RNA also must be lysed, and therefore would control for lysis. Similar techniques of introducing actual bacteria or viruses or other nucleic-acid-containing structures, which require lysis, can be used to control for lysis. These nucleic-acid-containing structures can be lyophilized, preserved with anhydrobiosis or other techniques until reconstituted by the sample or lysis reagents. Similarly internal controls which do not prove that lysis has occurred (such as pure DNA) can also be preserved and stored in the lysis chamber.

Internal or process control can be change from the preserve state (for instance lyophilized) by the sample if it is introduced into the chamber first, by the lysis reagents, by water contained in a separate fluid pouch, or any combination thereof.

Waste in Same Chamber, Contamination Prevention Via Aerosol Filter.

The same chamber or chambers that are used for lysis of the nucleic-acid-containing structures can also be used to contain the waste lysate material after the desired nucleic acids have been removed. The pressure created by the syringe can be used with for instance a silica-based membrane to capture the nucleic acids and then force the nucleic acid depleted lysate fluid back into the lysis chamber as waste. The lysis chamber can be sealed against leakage by the use of hydrophobic or chemically resistant porous material such as porous plastics (i.e. urethanes) which also offer distinct advantages over mechanical vents or physical openings since dust and moisture is kept out, there are no moving parts which can stick or only work in one direction and can be customized for self-sealing or color change options if the vent encounters moisture. For instance, porous material can be treated to produce hydrophilic properties allowing wicking of aqueous solutions or specially formulated to act as a self-sealing material in the presence of aqueous solutions. The self-sealing filters allow air to pass through but trap liquids, which may be infectious or contain nucleic acids, which can contaminate testing results.

Large Volumes

The microfluidic chip is scalable in terms of sample volume processed. This is of critical importance when trying to take rare, dilute or otherwise low nucleic acid copy number targets. The volume can be increased or decreased to match the volume required for meeting a lower limit of detection threshold in downstream processes. Very little fluid is lost, preserving lysis efficiency. The size of the chamber and any associated components, such as the stir bar or heating element or Peltier, or thermal insulation can be increased or decreased to accommodate both a larger sample volume and any larger amount of lysis reagents that may be required. The fluid pouches containing the lysis reagents can also be scaled contain the appropriate amount of fluid.

Sample Processing and Collection by the Syringe Glass Capillary

The lysis microfluidic chip can take input samples from a variety of sample collection devices. It can have a sample placed directly onto or into it, injected via syringe, deposited by pipette, deposited by a capillary tube, have a swab broken off in it or deposited sample via swab a stroke, absorbed onto an absorbent material, moved into the container by a stored vacuum such as a Vacutainer™ etc. The open design of the microfluidic chip can allow access from many different sample collection types directly into the lysis chamber. Additionally the pressure connection to the syringe can be used to create section to collect the sample into the lysis chamber. A microcontroller can oversee the administration of the sample into the lysis chamber and alert an operator when to place the sample onto the collection surface and simultaneously, or just prior to, begin creating suction with the syringe. The sample entry port can be shaped to easily collect the specific sample type. For instance a mating hole that friction seals or seals via a gasket to a syringe, pipette or capillary tube can be used. A sink like depression of appropriate size can also be used to collect various liquid samples, or even viscous samples with the use of the suction power provided by the syringe. The lysis chamber can be provided with an open top that can be sealed with an adhesive sealing surface in order to provide an area for depositing swab samples or EDTA treated capillary tube or for filter interconnect e.g. for obtaining plasma from whole blood samples.

Control Assembly

A microfluidic chip or system that comprises the microfluidic chip may be arranged such that it is in communication with a control assembly (e.g., FIG. 15B:1550). For example, the control assembly may be capable of modulating a source of cooling gas or liquid (e.g., altering, for example, the speed of a fan or controlling the flow of the gas or liquid via a controlled valve) and/or the output of a heater (e.g., via electrical input given by the controller to the heater). Moreover, the control assembly may be used for microfluidic chip or system automation, such that it may be programmed to, for example, automatically pre-process samples, perform a desired number of nucleic acid amplification cycles, execute a program that specifies thermal cycling parameters (e.g., temperatures, hold times, etc.), obtain measurements (if desired), digitize any measurements into data, and/or analyze data.

In some examples, a control assembly may control circuitry of a microfluidic chip that is capable of modulating a heater, and, thus, control the temperature of a sample during thermal cycling. In some examples, a control assembly may control circuitry of a microfluidic chip that is capable of modulating the flow of a cooling gas or liquid, and, thus, control the temperature of a sample during thermal cycling.

In examples where a control assembly acquires and analyzes data, the control assembly may communicate with an appropriate measurement microfluidic chip (e.g., a detector), digitize signals (i.e., raw data) obtained from the measurement microfluidic chip, and/or processes raw data into a readable form (e.g., table, chart, grid, graph or other output known in the art). Such a form may be displayed or recorded electronically or provided in a paper format.

A control assembly, for example, may include a processor which may or may not be included as part of a computer server. In cases where a computer server is absent, a control assembly may include a processor and any additional hardware (including hardware described herein) required for processor operation. An example computer server 1501 is shown in FIG. 15A. The computer server ("server") may be programmed, for example, to operate any component of a device or system and/or execute methods described herein. The server 1501 includes a central processing unit (CPU, also "processor") 1105 which can be a single core processor, a multi core processor, or plurality of processors for parallel processing. A processor used as part of a control assembly may be a microprocessor. The server 1501 also includes memory 1510 (e.g. random access memory, read-only memory, flash memory); electronic storage unit 1515 (e.g. hard disk); communications interface 1520 (e.g. network adaptor) for communicating with one or more other systems; and peripheral devices 1525 which may include cache, other memory, data storage, and/or electronic display adaptors. The memory 1510, storage unit 1515, interface 1520, and peripheral devices 1525 are in communication with the processor 1505 through a communications bus (solid lines), such as a motherboard. The storage unit 1515 can be a data storage unit for storing data. The server 1501 is operatively coupled to a computer network ("network") 1530 with the aid of the communications interface 1520. A processor (including those described herein), with the aid of additional hardware described herein, may also be operatively coupled to a network. The network 1530 can be the Internet, an intranet and/or an extranet, an intranet and/or extranet that is in communication with the Internet, a telecommunication or data network. The network 1530 in some cases, with the aid of the server 1501, can implement a peer-to-peer network, which may enable devices coupled to the server 1501 to behave as a client or a server. In general, the server may be capable of transmitting and receiving computer-readable instructions (e.g., device/system operation protocols or parameters) or data (e.g., sensor measurements, raw data obtained from detecting nucleic acids, analysis of raw data obtained from detecting nucleic acids, interpretation of raw data obtained from detecting nucleic acids, etc.) via electronic signals transported through the network 1530. Moreover, a network may be used, for example, to transmit or receive data across an international border.

The server 1501 may be in communication with one or more output devices 1535 such as a display or printer, and/or with one or more input devices 1540 such as, for example, a keyboard, mouse, or joystick. The display may be a touch screen display, in which case it may function as both a display device and an input device. Different and/or additional input devices may be present such an enunciator, a speaker, or a microphone. The server may use any one of a variety of operating systems, such as for example, any one of several versions of Windows, or of MacOS, or of Unix, or of Linux.

The storage unit 1515 can store files or data associated with the operation of a device or method described herein.

The server can communicate with one or more remote computer systems through the network 1530. The one or more remote computer systems may be, for example, personal computers, laptops, tablets, telephones, Smart phones, or personal digital assistants.

In some situations a control assembly includes a single server 1501. In other situations, the system includes multiple servers in communication with one another through an intranet, extranet and/or the Internet.

The server 1501 can be adapted to store device operation parameters, protocols, methods described herein, and other information of potential relevance. Such information can be stored on the storage unit 1515 or the server 1501 and such data can be transmitted through a network.

Devices and/or systems as described herein can be operated and methods described herein executed by way of machine (or computer processor) executable code (or software) stored on an electronic storage location of the server 1501, such as, for example, on the memory 1510, or electronic storage unit 1515. During use, the code can be executed by the processor 1505. In some cases, the code can be retrieved from the storage unit 1515 and stored on the memory 1510 for ready access by the processor 1505. In some situations, the electronic storage unit 1515 can be precluded, and machine-executable instructions are stored on memory 1510. Alternatively, the code can be executed on a second computer system 1540.

Aspects of the devices, systems, and methods provided herein, such as the server 1501, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g. read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical, and electromagnetic waves, such as used across physical interfaces between local devices, through wired and optical landline networks and over various air-links. The physical elements that carry such waves, such as wired or wireless likes, optical links, or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, tangible storage medium, a carrier wave medium, or physical transmission medium. Non-volatile storage media can include, for example, optical or magnetic disks, such as any of the storage devices in any computer(s) or the like, such may be used to implement the system. Tangible transmission media can include: coaxial cables, copper wires, and fiber optics (including the wires that comprise a bus within a computer system). Carrier-wave transmission media may take the form of electric or electromagnetic signals, or acoustic or light waves such as those generated during radio frequency (RF) and infrared (IR) data communications. Common forms of computer-readable media therefore include, for example: a floppy disk, a flexible disk, hard disk, magnetic tape, any other magnetic medium, a CD-ROM, DVD, DVD-ROM, any other optical medium, punch cards, paper tame, any other physical storage medium with patterns of holes, a RAM, a ROM, a PROM and EPROM, a FLASH-EPROM, any other memory chip or cartridge, a carrier wave transporting data or instructions, cables, or links transporting such carrier wave, or any other medium from which a computer may read programming code and/or data. Many of these forms of computer readable media may be involved in carrying one or more sequences of one or more instructions to a processor for execution.

Sources and Samples

The methods and devices disclosed herein may be used to isolate and/or purify molecules from a sample. Isolation and/or purification of molecules from the sample may comprise lysing one or more nucleic acid-containing structures. Exemplary nucleic acid-containing structures include, but are not limited to, cells (e.g., eukaryotic cells, prokaryotic cells, fungi), organelles and viruses. Samples containing nucleic acid-containing structures lysed in a method of the disclosure may be obtained from a variety of sources. For example, a sample may be obtained from biological sources with non-limiting examples that include humans, animals, plants, fungi, other eukaryotes, bacteria, and viruses. Animals may include, but are not limited to, mammals, avians, reptiles, and amphibians. Mammals may be humans or non-human primates. Alternatively, mammals may be dogs, sheep, cows, cats, rodents, horses or rabbits. Samples may be obtained from two or more different sources. The two or more different sources may be from different species. The two or more different sources may be from the same species. Moreover, nucleic acid-containing structures may be found, for example, in a number of biological fluids (e.g., blood, urine, spinal fluid, cerebrospinal fluid, synovial fluid, amniotic fluid, semen, vaginal discharge, saliva, etc.), solid tissue samples, feces, hair, tissue cultures, sections, smears, or combinations thereof.

Other types of biological samples may include food products such as vegetables, dairy items, meat, meat by-products, and waste. Samples may also be obtained from non-living sources with non-limiting examples that include soil, water, sewage, cosmetics, agricultural specimens, industrial specimens, air filter specimens, and air conditioning specimens.

Samples may be obtained from healthy subjects. Samples may be obtained from non-healthy subjects. The non-healthy subjects may be suffered from a disease or condition (e.g., cancer, pathogenic infection, autoimmune disorder, inflammatory disease, etc).

Applications

Devices and methods of the disclosure may be useful in a variety of applications, either separately or in combination. In some examples, devices and/or methods of the disclosure may be used in a biomedical application with non-limiting examples that include genetic testing (for example, to assess a subject's risk of presenting a genetic disease, such as, for example, cancer), tissue typing, disease diagnosis, disease staging, and/or disease detection. Devices and methods described herein may be utilized, for example, to detect a pathogen, with non-limiting examples that include bacteria (e.g., *Mycobacterium, Streptococcus, Salmonella, Shigella, Staphylcococcus, Neisseria, Pseudomonads, Clostridium*, or *E. coli*), yeast, fungi, virus, eukaryotic parasites, etc; or an infectious agent, with non-limiting examples that include influenza virus, parainfluenza virus, adenovirus, rhinovirus, coronavirus, hepatitis viruses A, B, C, D, E, human immunodeficiency virus (HIV), enterovirus, human papillomavirus (HPV), cytomegalovirus, coxsackievirus, herpes simplex virus, Epstein-Barr virus, or other viruses associated with a sexually transmitted disease. Additionally, devices and methods described herein may also be used in forensic applications such, such as, for example, genetic fingerprinting in criminal cases, parental testing, environmental surveillance, and anti-bioterrorism.

Moreover, methods and devices of the disclosure may also be useful in a number of techniques found in biomedical research environments, with non-limiting examples of such techniques that that include the rapid production of DNA, DNA or RNA sequencing, DNA cloning, sequence-tagging, studies of DNA from ancient sources, studying patterns of gene expression, and answering questions in evolutionary biology or archaeology.

A microfluidic chip may incorporate micromachined electrodes spaced less than 100 micrometers apart on a silicon substrate are used to lyse cells as disclosed in U.S. Pat. No. 6,287,831 B1 to Tai et al. In some cases, a chip may comprise a mechanism for radiating magnetic beads in a reaction chamber with a laser as described in US 2007/0134809 (Cho et al.). In some cases, a chip may also comprise a mechanism for use of a single electric pulse of between 10 milliseconds and 10 microseconds to lyse cells and lysate is transferred into a microcollection device as disclosed in US 2004/0058423 A1 (Albritton et al.). In some cases, a microfluidic chip may incorporate microfluidic cartridge and associated method for selective lysis of and extraction of DNA from cell mixtures as disclosed in US 2005/0064598 A1 (Yuan et al.).

Kits

In some cases a microfluidic chip is part of a kit for lysing a sample. The kit may also comprise one or more lysis buffers. The kit may comprise one or more lyophilized lysis reagents. The kit may comprise at least one PCR reagent (e.g., polymerase, dNTPs, buffer, Mg, primers, probes, TaqMan probes, intercalating dyes, etc.). In some cases, the kit comprises at least one pump which maybe a syringe pump. Some kits may also have a device for sample purification. In some cases, a kit also comprises a magnetic device and/or mechanical elements (e.g., stir bars, beads, etc.).

The term "about," as used in this disclosure, generally refers to a range that is 15% greater than or less than a stated numerical value within the context of the particular usage. For example, "about 10" would include a range from 8.5 to 11.5.

EXAMPLES

The following illustrative examples are representative of embodiments of the software applications, systems, and methods described herein and are not meant to be limiting in any way.

Example 1

Microfluidic Chip Comprising Lysis/Mixing Chamber and Magnetic Stir Bar

FIG. 1 shows a schematic of an exemplary microfluidic chip. The microfluidic chip is assembled via converted-tape technology and thus comprises a series of layers 140. The microfluidic chip is used for sample lysis and comprises a lysis/mixing chamber 120 and magnetic stir bar 130. The microfluidic chip is designed with thermal insulation air grooves 150 for thermal isolation of the chamber 120 from the rest of the chip during lysis. The microfluidic chip also contains an input port 190 for introducing a sample or reagent into the chamber 120. The microfluidic chip also contains a vent 180 for releasing air or fluids from the chamber 120. The raw sample lysis/mixing chamber 120 is designed to fit a 1-inch square for resistive heater 160 using a converted tape technology a set of techniques known in the art to cut channels, chambers and functional units into strips of tape with dies, lasers or other means in individual pieces of tape and then laminating them together to form a compact device. The thermal design is meant to raise the temperature of the sample and keep it at a stable raised temperature for a period of time. This can cause thermal lysis, provide the optimum temperature for chemical or lysis or enzymatic digestion, and optimize the lysis process. The resistive heater 160 is coupled to a thermal transducer 170. Mixing with a magnetically coupled stir bar 130 is incorporated for creating a well-mixed lysis environment. The microfluidic chip is used with a syringe 110, magnet 191 and motor 192. The stir-bar 130 and rotating magnetic field can also be used to cause mechanical lysis either by the stir bar acting on particles, nucleic-acid-containing structures (e.g., cells), magnetic particles (see FIG. 2) or any combination thereof. Alternatively the lysis can proceed by the sample and any lysis agents being mixed by shuttling back and forth between the two chambers. Thorough mixing and temperature homogenization of the sample with any chemical or mechanical lysis reagents occurs by pressure driven flow back and forth between the two (or multiple) chambers. In addition the liquid can pass through filters designed to mechanically lyse (see FIG. 3).

Example 2

Microfluidic Chip Comprising Lysis/Mixing Chamber and Magnetic Beads

FIG. 2 shows an illustration of lysis method by use of granular particles such as magnetic beads 204 to generate friction force and collisions between the cells and granular particles (magnetic beads) in the solution. Glass beads can also be used to achieve the same effect. The raw sample to be lysed can be filtered to remove contaminants before being transported to the lysis chamber 203 by applying positive pressure. Positive pressure can be applied for instance, by means of a syringe with a liner actuator 201. A filter membrane 202 may be present, which can also be interchanged for a specific application such as binding, adsorption to the sample or other chemical interaction mechanisms. For instance, after lysis a different set of filter membrane can be used to specifically bind the target by applying negative pressure with the syringe or with linear actuator and use of the valve to control the flow. A valve 205 maybe present to drain the sample from the lysis chamber.

Example 3

Figure 3:
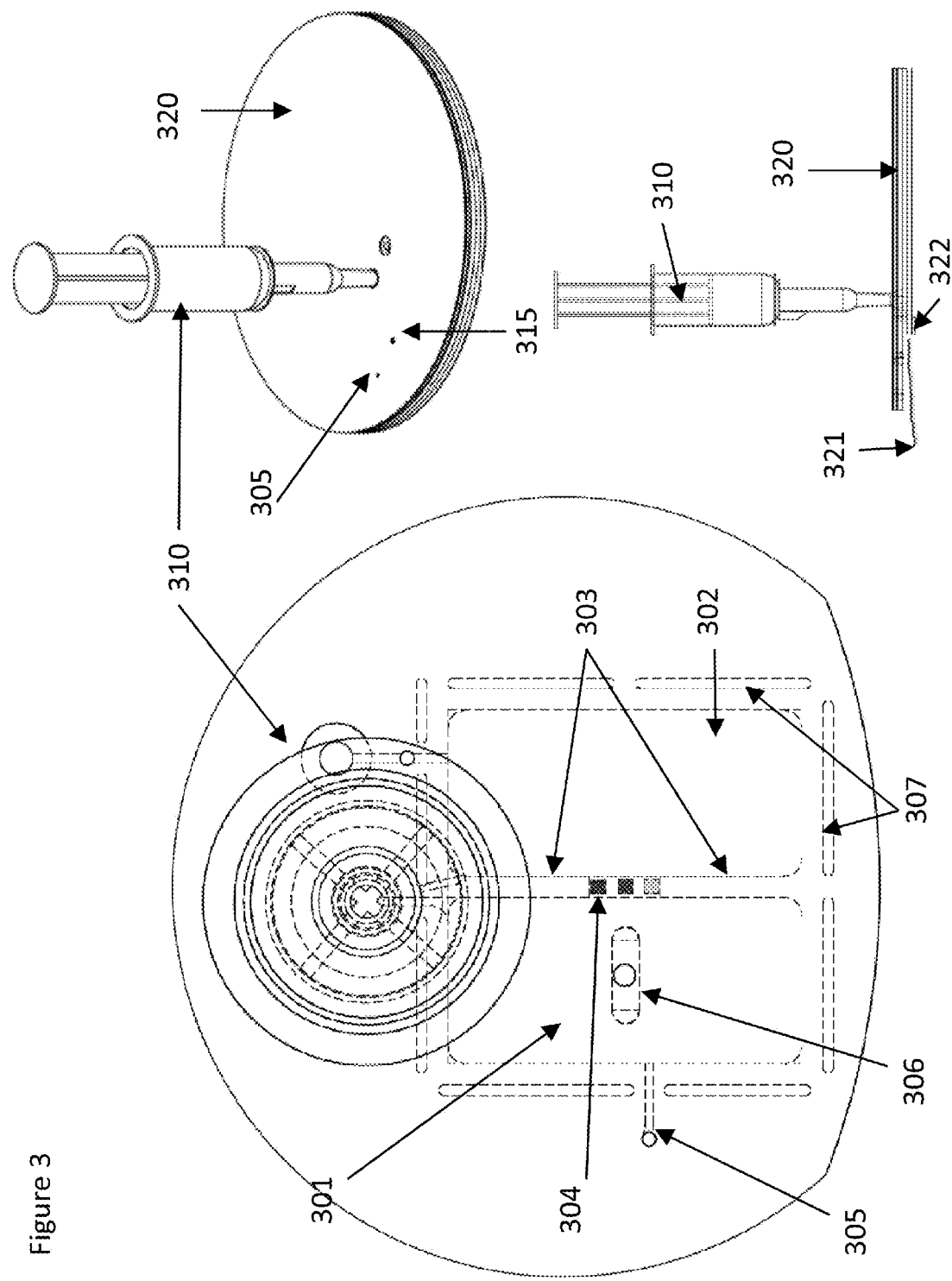
FIG. 3 is a multi-view schematic of an exemplary microfluidic chip described herein, comprising heating assembly, thermally insulative grooves, stir bar and filters across chamber walls.

Microfluidic Chip Comprising Lysis/Mixing Chambers, Magnetic Stir Bar and Micro Channel Filters FIG. 3 shows mechanical lysis method using filter like micro channels filters 304 across the chamber wall 303 with two chamber mixing 301, 302 and coupled to micro stir bar 306 mixing to ensure a complete homogenized sample lysis reagent mixture. The filter channels 304 have contraction structures through which the pressure driven flow for the particles to be lysed is achieved. The particles to be lysed are subjected to shear and frictional forces induced by entering the contractions. Sharp nanostructure can be added to the contraction sidewalls to penetrate the particle membrane and high flow rates/high pressure to increases the frictional forces and facilitates lysis. The microfluidic chip also contains an input port 305, insulative air grooves (e.g., apertures) 307, vent 315, resistive heater 322 and thermal transducer 321. The microfluidic tape is assembled via converted-tape technology and thus comprises a series of layers 320. The microfluidic chip is used with a syringe 310.

Example 4

Microfluidic Chip Comprising Chambers and Mixing Channel

Figure 4:
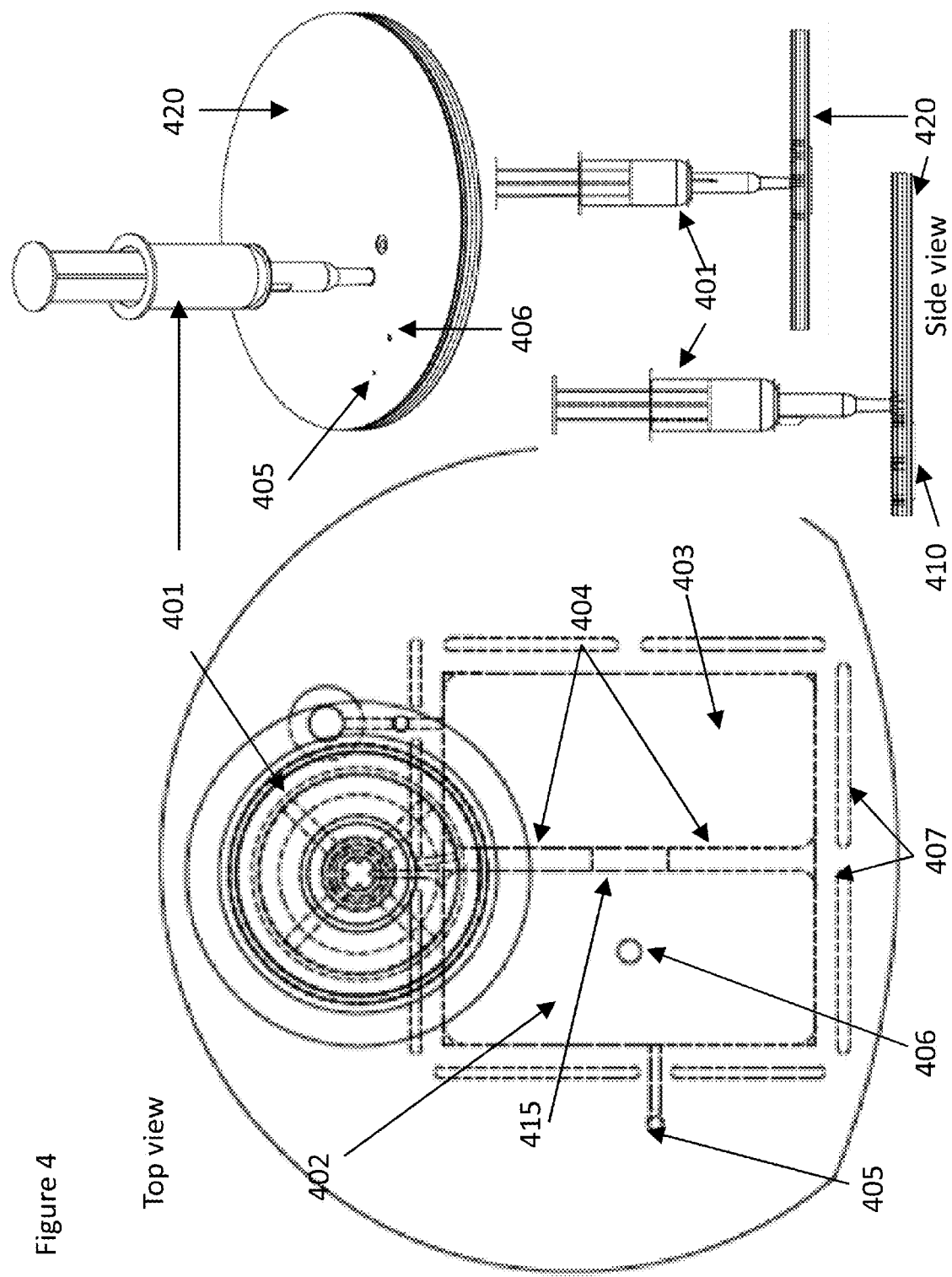
FIG. 4 is a multi-view schematic of an exemplary microfluidic chip described herein, comprising heating assembly and thermally insulative grooves.

FIG. 4 shows a microfluidic chip for use in lysis methods comprising heat and chemical lysis. The microfluidic chip contains two chambers 402, 403 separated by a chamber wall 404 and a mixing channel 415. The mixing is achieved by shuttling the sample, lysis reagents and other lysis additives back and forth between the two chambers 402, 403 through a wide channel 415 that connects the two chambers. The advantage of thermal lysis is that 5 min exposure at 70° C. in presence of lysing chemical such as Triton X 100, SDS, chaotropic salts such as guanidinium thiocyanate and guanidinium chloride lyse is sufficient to disrupt membrane of the particle to be lysed without damaging the nucleic acids. The microfluidic chip also contains an input port 405, vent 406, and resistive heater 410. The two chambers 402, 403 are insulated from the rest of the chip by a plurality of insulative grooves (e.g., apertures) 407. The microfluidic tape is assembled via converted-tape technology and thus comprises a series of layers 420.

Example 5

Microfluidic Chip Comprising Staggered Herringbone Mixer

FIG. 5 shows a microfluidic chip comprising a staggered herringbone mixer for use in sample lysis. Channel dimensions, fluid viscosities, pressure drop and other parameters define the mixing ratio of different reagents and the sample. The description and mixer operation as follows: the raw sample is inserted into chamber #1 (501) while the lysis reagents are added into chamber #2 (502). Suction from chamber #5 (505) (or pressure exerted onto 1 and 2) creates equal pressure drop across the fluid paths. The lysis reagents and the sample are drawn into the staggered herringbone-mixing channel (503) at a ratio determined by the size of channels and the pressure used. Fluids combine and mix in the staggered herringbone-mixing channel 4 (504), which is a 3-D pattern, etched on a thicker channel layer. For more thorough mixing the staggered herringbone structures is made longer so that the fluids interact over a greater distance thereby increasing the resident time. The mixed solution is moved into chamber #5 (505). Then the organic solvents reagents such as isopropyl alcohol (IPA) or ethyl alcohol (EtoH) required for sample of interest precipitation and binding it to extraction support, is pipetted into chamber #6 (506). Suction from chamber #9 (509) (or pressure exerted onto chamber 5 (505) and 6 (506)) create pressure drop across paths and the mixed solution, IPA or EtOH are drawn and mixed in channel 8 (507, 508) and drawn to chamber #9 (509) this way, the lysate is transported into final chamber 9 (509) and is ready for downstream use. Thermal and chemical lysis can be accomplished by heating the herringbone-mixing channel 4 (504) with a resistive heater as the sample and lysis reagents are mixing.

Example 6

Microfluidic Chip Comprising Staggered Herringbone Mixer

Figure 6:
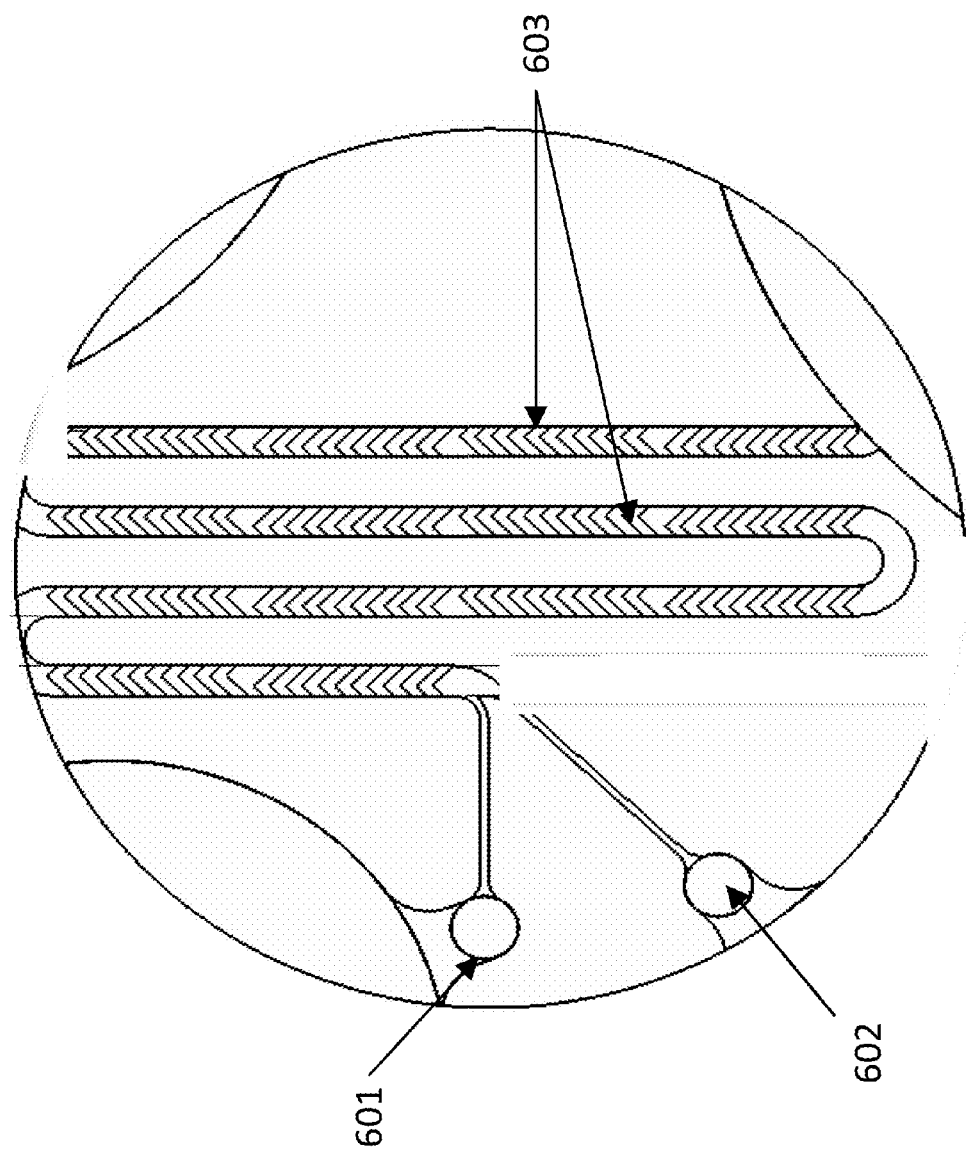
FIG. 6 is a schematic of a serpentine herringbone mixer.

FIG. 6 shows a close up microfluidic chip layout with staggered herringbone mixer 603 for sample preparation concept. The sample undergoes chemical lysis in the mixer or both chemical lysis and thermal lysis, which is achieved by resistive heating of the herringbone-mixing channel 603. An individual staggered herringbone mixer with predefined staggered herringbone mixer dimensions calculated for a 90% mixing of whole blood samples with most typical lysis buffers. To achieve 100% mixing the mixer is made longer serpentine to increase the resident times of the reagents, samples and chemicals to be mixed and also to occupy smaller footprint. The microfluidic chip contains two entry spots 601, 602 into the staggered herringbone mixer. A blood sample can be enter the staggered herringbone mixer 603 via the entry spot 601. Lysis and binding buffers can enter the staggered herringbone mixer 603 via a second entry spot 602.

Example 7

Microfluidic Chip Comprising Lysis Chambers, and Thermal Transducers

Figure 7:
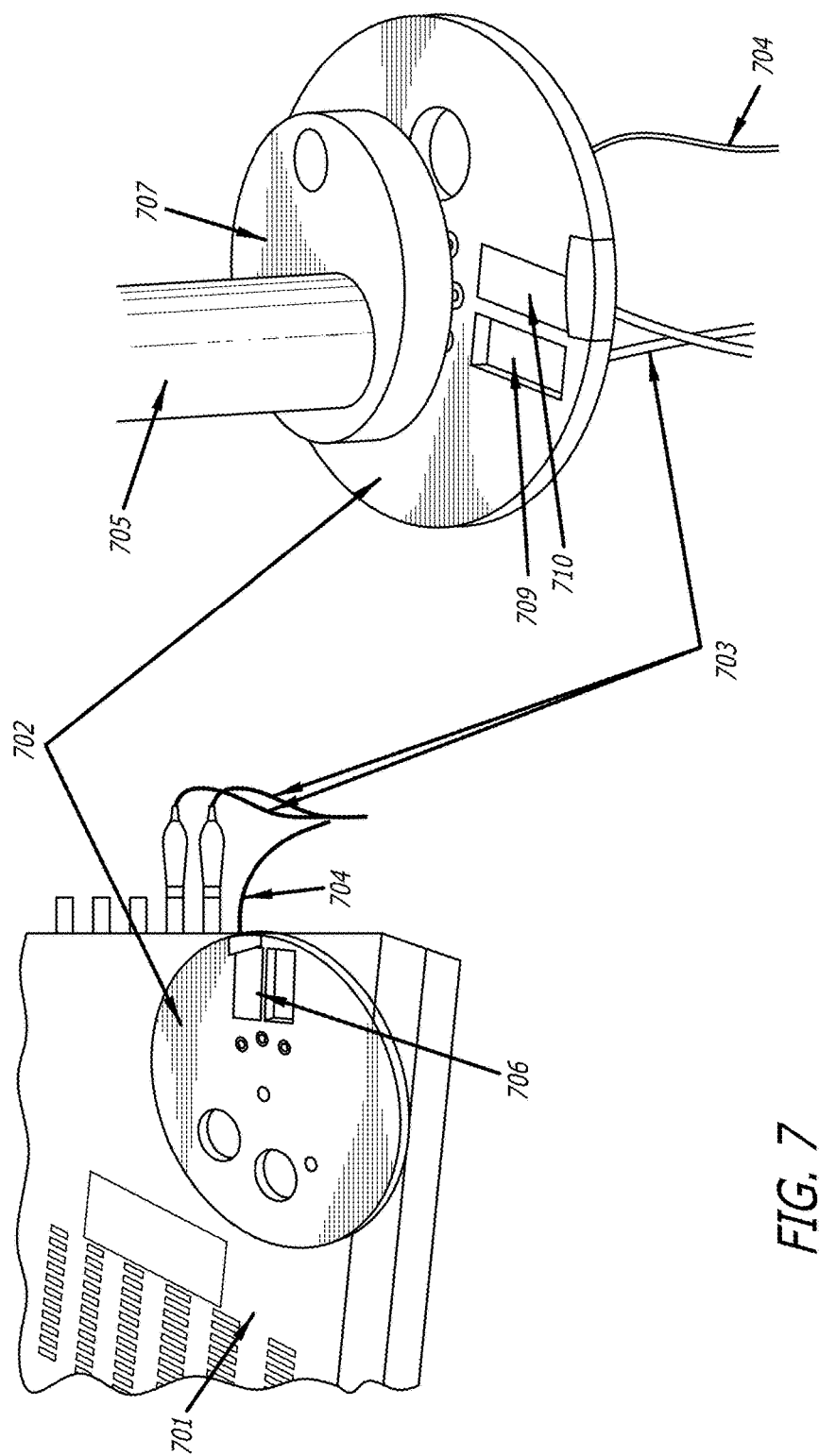
FIG. 7 is a multi-view depiction of an exemplary microfluidic chip described herein.

FIG. 7: shows the lysis chambers of a microfluidic chip 702. Since prolonged heating or higher amount of heat, however, may cause irreversible denaturation of superhelical DNA. The assembly is fitted with the thermal transducer 704 for temperature control feedback and monitoring of the heat generated by use of the power supply 701. The mixing is achieved in the two chambers 709 and 710 by shuttling back and forth the sample and lysis mixture 706 while heating the two chambers. The resistive heaters 703 are attached under the chamber with a pressure sensitive heat conductive adhesive in order to make an optimal thermal contact. The chip also has a disposable mount 707 and a syringe holder 705.

Example 8

Microfluidic Chip for Chemical and Thermal Lysis

Figure 8:
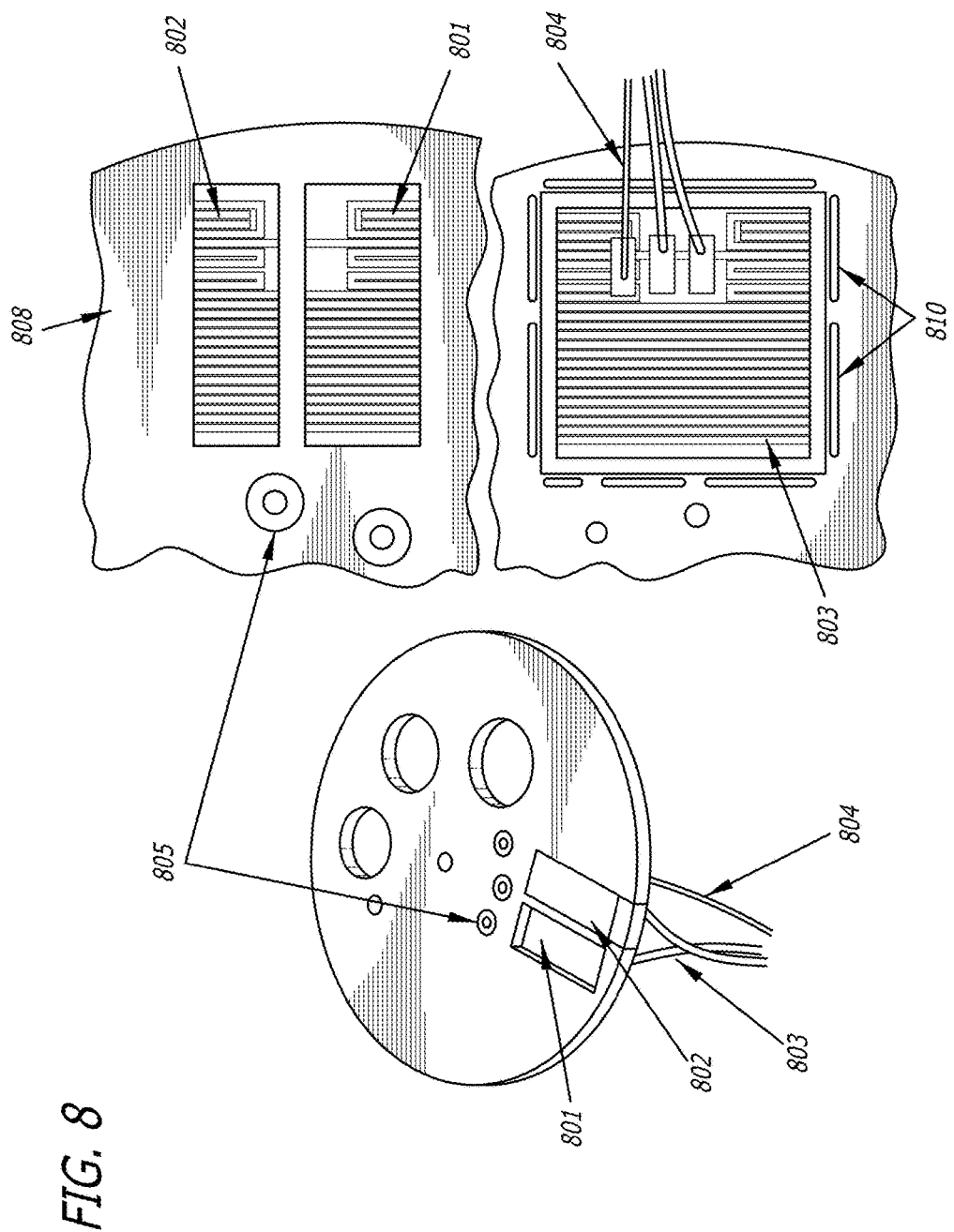
FIG. 8 is a multi-view depiction of an exemplary microfluidic chip described herein.

FIG. 8 shows a microfluidic chip for chemical and thermal lysis fitted with a thermal transducer 804 to control the temperature from the heat from a resistive heater 803 attached at the bottom of the chamber with a pressure sensitive heat conductive adhesive. The chip shows individual chambers 801 and 802, input/output ports 808 and 805, chambers and insulative thermal grooves 810 for thermal isolation and ambient air insulation of the lysis/mixing chambers from the rest of the components or disposable peripherals that maybe located on the chip and would act as heat sink with penalties such as high power requirement for heating and longer heating times.

Example 9

Microfluidic Chip Comprising Chambers, Insulative Grooves and Electrodes

Figure 9:
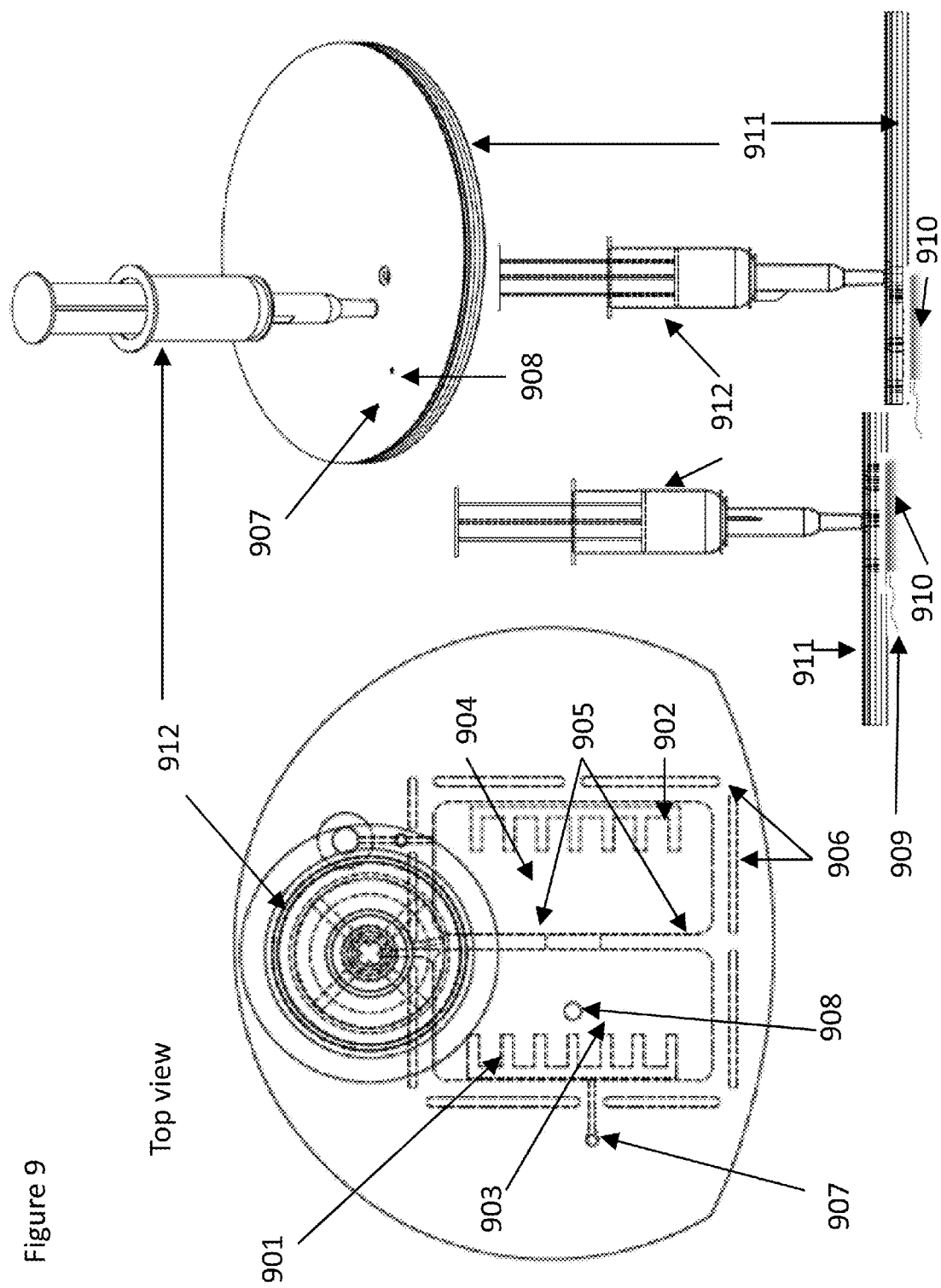
FIG. 9 is a multi-view schematic of an exemplary microfluidic chip described herein, comprising assembled layers with heating assembly, thermally insulative grooves, and electrodes.

FIG. 9 shows a microfluidic chip for use in electrical lysis through electroporation of cells, bacteria, spores cells, etc. The microfluidic chip contains an array of electrodes 901, 902 shaped such as three-dimensional cylinders to increase the electric field strengths or saw-tooth shapes of the microelectrodes for nonuniform electric field lysis. The cylindrical shape provides more volume in which the electric field affects the cell membrane/wall. Other variations can be used, for instance, an electric field can be generated by a platinum wires inserted into microfluidic chambers/reservoirs connected by a channel with narrowing geometry at least one order of magnitude in width to intensify the electric field and lyse the cells.

The microfluidic further comprises two chambers 903, 904 separated by a chamber wall 905. Each chamber 903, 904 contains an electrode 901, 902. The chambers 903, 904 are surrounded by one or more apertures 906. An input port 907 enables entry of a sample to a chamber 903. The microfluidic chip further comprises a vent 908. The microfluidic chip further comprises a thermal transducer 909 and a resistive heater 910. As shown in FIG. 9, the microfluidic chip is assembled in layers 911. A syringe 912 can be used in conjunction with the microfluidic chip.

Example 10

Microfluidic Chip Comprising Chamber and Magnetic Beads

Figure 10:
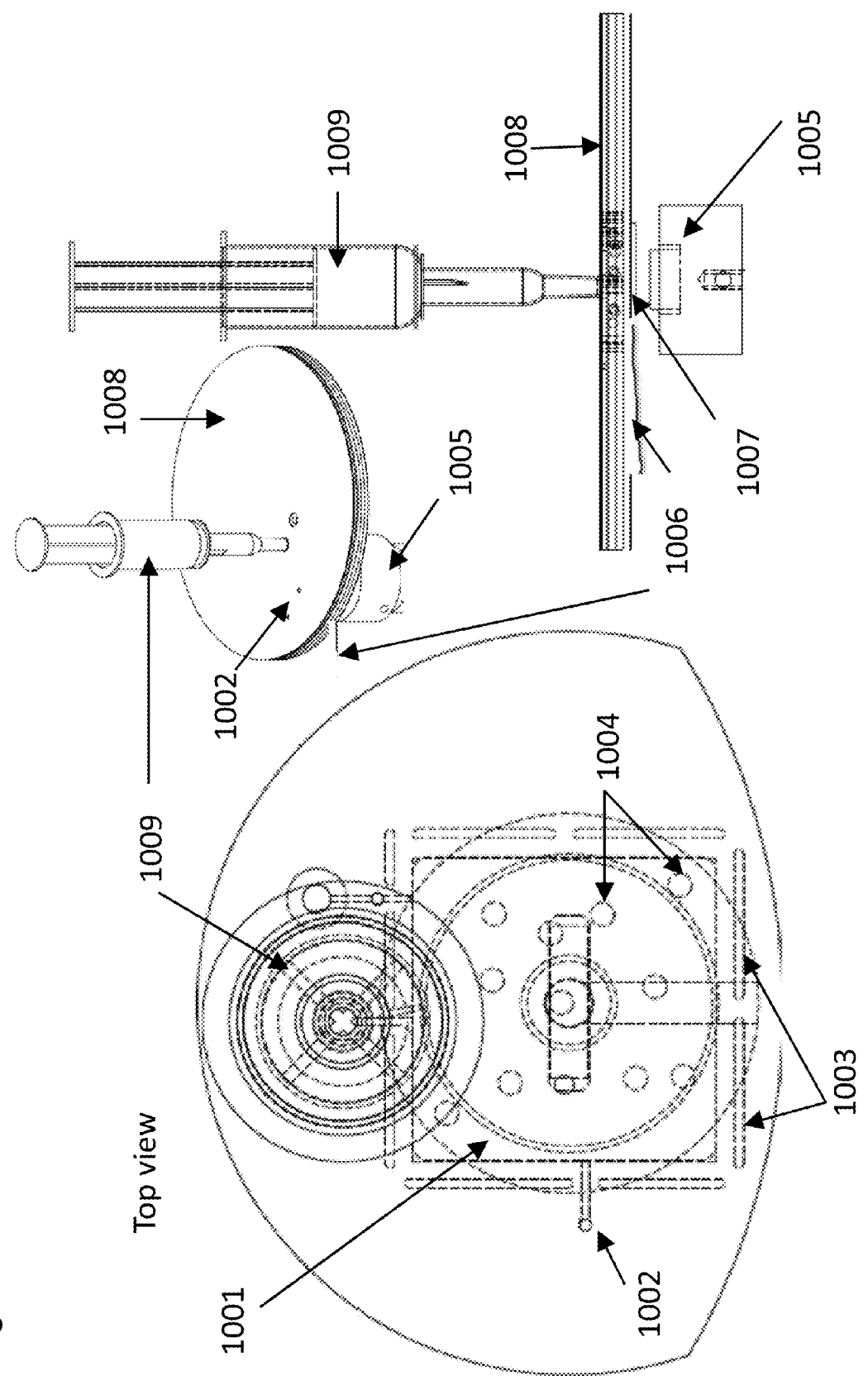
FIG. 10 is a multi-view schematic of an exemplary microfluidic chip described herein, comprising assembled layers with heating assembly, thermally insulative grooves, and granular particles.

FIG. 10 shows a microfluidic chip for use in lysis methods comprising granular particles such as magnetic beads to generate friction force and collisions between the cells and granular particles (magnetic beads) in the solution. The friction and collisional forces are generated by electromagnets placed below the lysis chamber or close proximity with optimal orientation. The mixing and homogenization of the sample and lysis chemical mixture is achieved by the vigorous agitation of the magnetic beads. For hard to lyse samples such as sputum samples, heating or boiling is required which is achieved here by attaching at the bottom of the chamber a pressure sensitive heat conductive adhesive with a thermal transducer to control the temperature from the resistive heater. The chambers input/output ports and insulative thermal grooves for optimal thermal management.

The microfluidic chip comprises a chamber 1001, input port 1002, electromagnet 1005, thermal transducer 1006, and resistive heater 1007. The chamber 1001 also contain one or more magnetic beads 1004. The chamber is surrounded by one or more apertures 1003. The microfluidic chip is assembled in layers 1008. A syringe 1009 is used in conjunction with the microfluidic chip.

Example 11

Microfluidic Chip Utilizing Laser Beam Lysis

FIG. 11 shows schematic for a chip 1110 utilizing a lysis method by use of focused laser beam 1101 to alter and/or to ablate cellular and tissue samples as well as intracellular organelles or by forming plasma generating shock wave and bubbles, which expand and collapse to cause lysis, in a lysis chamber 1104, wherein the objective lens of the laser is at 1102, and the focal point 1103.

Example 12

Microfluidic Chip Comprising Chamber and Fluid Pouches

Figure 12:
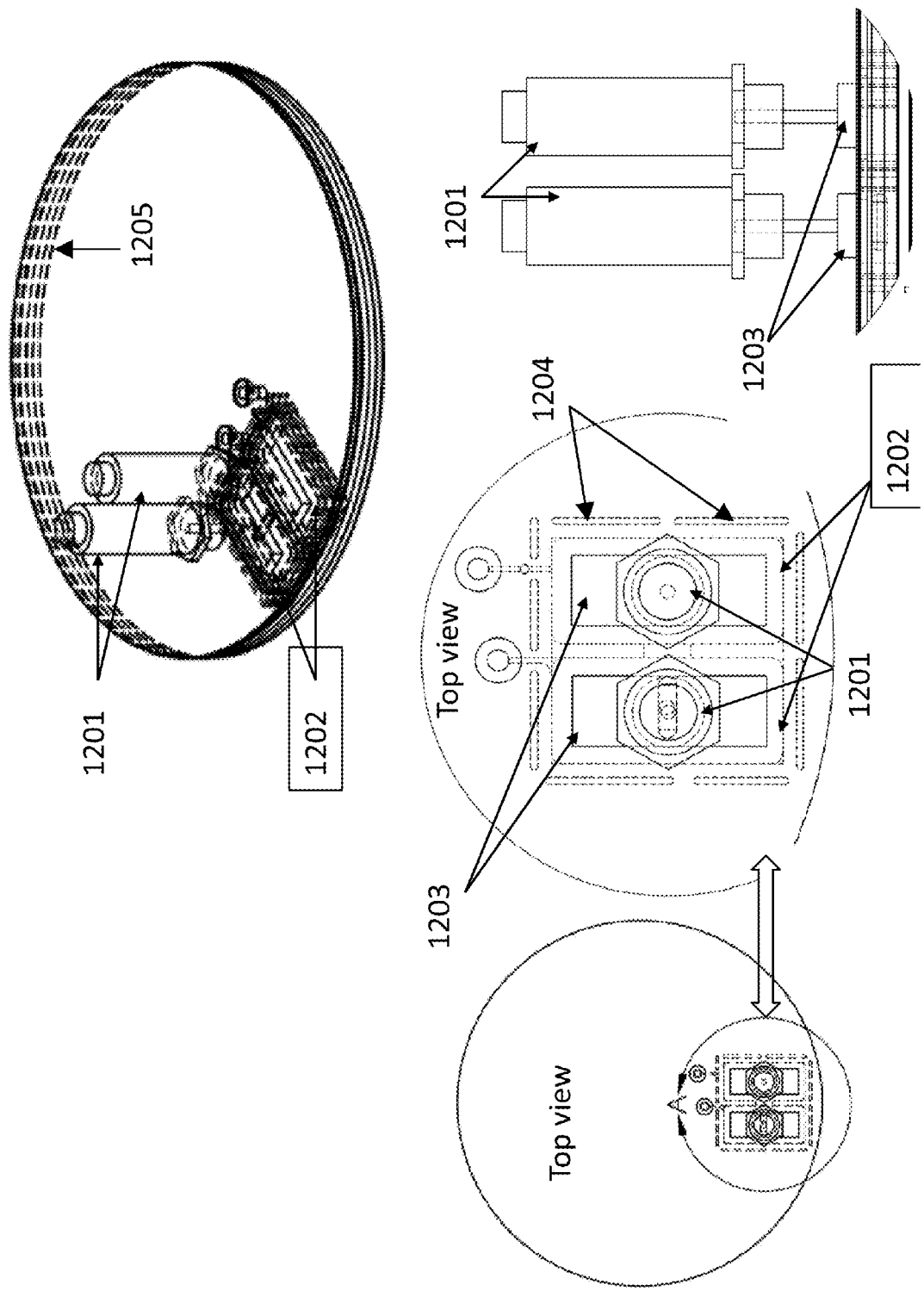
FIG. 12: is a multi-view schematic of an exemplary microfluidic chip described herein, comprising thermally insulative grooves, and fluid pouches

FIG. 12 shows one or multiple fluid pouches from which the fluid enters at the appropriate time into the chamber via microcontroller controlled electromechanical bursting of the fluid pouches allowing the fluid to enter the chamber via the fluid pouch's own channel or a shared input channel. The filling of the lysis chamber with sample or lysis buffer can be accomplished by gravity or by simultaneously to, or just prior to, fluid presentation at the chamber, retracting the syringe to create suction in the chamber. The movement of the lysis buffers and sample are actuated by pressure from the coupled syringe or a linear actuator.

The microfluidic chip comprises two chambers 1202, electromechanical actuator 1201, fluid pouches 1203, and apertures 1204. The apertures 1204 surround the chambers 1202. The fluid pouches 1203 can be located within the chambers 1202. Alternatively, the fluid pouches 1203 are located within close proximity to the chambers 1202. The microfluidic chip is assembled in layers 1205.

Example 13

Microfluidic Chip Comprising Lysis/Mixing Chamber and Magnetic Stir Bar

Figure 13:
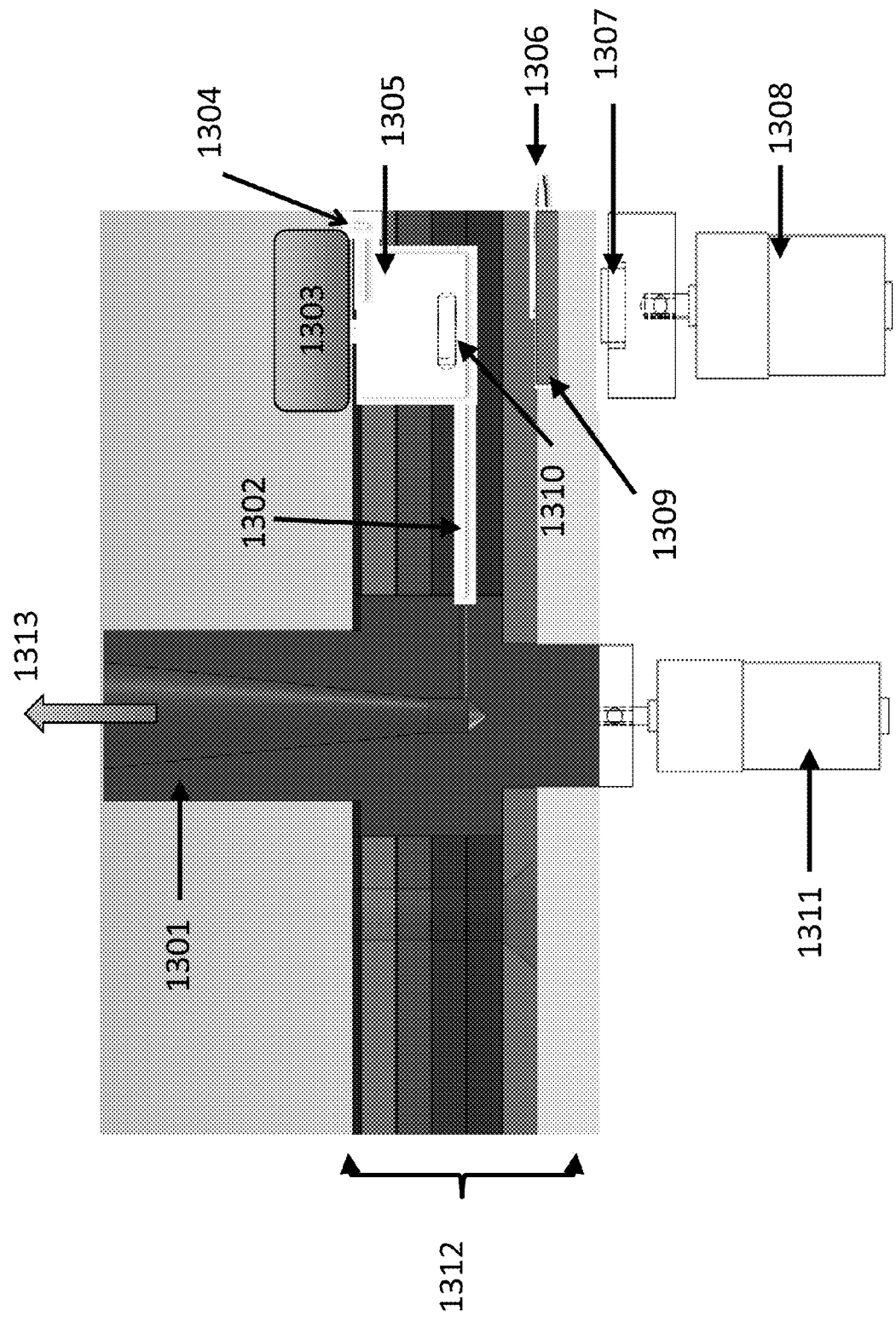
FIG. 13 is a schematic displaying an exemplary microfluidic chip described herein.

FIG. 13 shows a microfluidic chip for use in thermal and/or chemical lysis with optional stir bar mixing. The lysis reagent is premeasured and stored in fluid pouches, and is released into the chamber via microcontroller controlled electromechanical bursting of the fluid pouches as shown in FIG. 12. The microfluidic chip is fitted with an inexpensive valve that is injection-molded from soft yet seal compliant material such as Teflon, although other material such as derlin, acrylic etc can be used. For precise fluid manipulation the valve may be coupled to a stepper motor, which is used for rotation and precision in indexing the valve location. The whole process of fluid pouches bursting and valve indexing can be automated via microcontroller. The valve interacts with the syringe, and channels the pressure change to the fluid and directs the fluid flow. A high precision of fluid flow can be achieved by combining a hi-resolution linear actuator on the syringe with low dad volume fluid handling in the microfluidic chip cartridge and valve body. A precision fluid volume container is used to hold a precise amount of fluid in the valve body for transfer from one chamber to another.

The microfluidic chip comprises a valve body 1301, fluidic channel 1302, fluid pouch 1303, sample inlet/vent port 1304, lysis chamber 1305, thermal transducer 1306, magnet 1307, motor 1308, resistive heater 1309, stir bar 1310, and stepper motor 1311. The microfluidic chip is assembled in layers 1312. The microfluidic chip further comprises a vent/port that can be accessed by a syringe 1313.

Example 14

Lysis Device Comprising Tubing Wrapped Around a Cartridge Heater/Chiller

Figure 14:
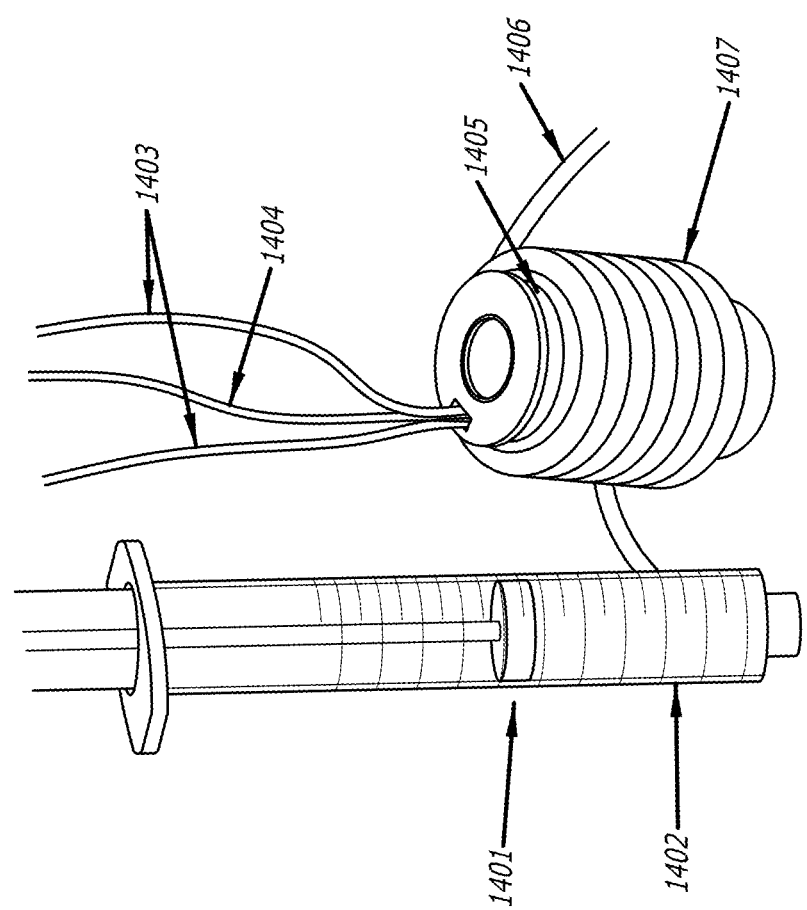
FIG. 14 is a depiction of an exemplary microfluidic chip described herein comprising a tubular chamber tubing wrapped around a cartridge heater/chiller.

FIG. 14 shows a lysis device consisting of tubing 1407 wrapped around a cartridge heater/chiller 1405. This lysis device connects to a sample collection device upstream for sample input (e.g., blood, sputum . . . ). The sample collection device contains a plunger 1401 and sample holder/input 1402. The lysis device connects to a microfluidic sample analysis chip downstream (e.g., Purification and amplification) 1406. A collected sample is inserted into the tubing utilizing positive or negative pressure provided from at least one end of the system. The tubing will contain reagents in liquid or lyophilized form or coated/adsorbed on the sidewalls. Cycling the pressure in the system moves the sample and lysis reagents back and forth. Cycling effectively, use of optimal tube diameter, increasing the fluid flow path length and the fluid velocity will accelerate the mixing process. The lysis process may also be accelerated by mixing and heating or cooling the tubing 1407 with the wrapped cartridge 1405 with a thermal transducer 1404. The heating or cooling of the tubing 1407 can be facilitated with the use of heater leads 1403. The lysed sample (lysate) is then be moved for downstream process by the same positive/negative pressure system (possibly a syringe). The lysis device consists of: 1) Cartridge heater/chiller 1405 coupled to a thermal transducer 1404 for temperature control of sample and/or reagents in the wrapped tubing; 2) tubing 1407 containing the sample, reagents, and/or lyophilized reagents is wrapped around the cartridge heater/chiller 1405; 3) tubing 1407 can be made of any material known in the art (e.g., polymers, metals, rubbers); 4) reagents may be freeze-dried (lyophilized) on sidewalls of tubing; 5) tubing is of an appropriate diameter and length to promote effective mixing of sample, reagents, and/or particulate solid and/or a lyophilite, wherein the total tubing inner volume capacity may be more or less than the volume of all reagents and sample; 6) plunger or linear actuator or other means to provide positive/negative pressure cycles to induce fluid flow and fluid cycling back and forth to promote mixing by increasing path length and fluid velocity located at least one end tubing lysis device.

Example 15

Microfluidic Chip Comprising Multiple Chambers and Pouches

FIG. 16 depicts an exemplary microfluidic chip. The microfluidic chip as depicted in FIG. 16 comprises a sample input chamber 1601, two chambers 1602, 1604 containing fluid pouches 1603, elution chamber 1606, and hold chamber 1605. The fluid pouches 1603 within the chambers 1602, 1604 can be ruptured, punctured or burst by a motor or other means. A glass frit or silica membrane 1607 is embedded into the microfluidic chip. The microfluidic chip also comprises a motor 1614 for valve rotation. The microfluidic chip further comprises gels and/or heaters 1612, 1613. The gel/heater 1612 contain a heater 1608, thermal transducer 1609 and thermosensitive valves 1611. The thermosensitive valves 1611 are gel valves that shrink at room temperature. The gel heater 1613 contains a heater 1615, thermal transducer 1616 and thermosensitive valves 1610. The thermosensitive valves 1610 are gel valves that expand upon heating/

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

What is claimed is:
1. A microfluidic chip comprising:
   a. a chamber which comprises at least one stir bar or a plurality of granular particles;
   b. a thermal device in thermal contact with the chamber; and c. at least one insulative groove within the surface of the chip, wherein the at least one insulative groove is configured such that during operation of the chip, ambient air enters the at least one insulative groove and insulates the chamber, and wherein the at least one insulative groove is a plurality of grooves positioned around the chamber.

2. The microfluidic chip of claim 1, wherein the thermal device is a heater or a cooler.

3. The microfluidic chip of claim 1, wherein the at least one insulative groove is nine insulative grooves.

4. The microfluidic chip of claim 1, wherein the stir bar is composed of magnetic material.

5. The microfluidic chip of claim 1, wherein the microfluidic chip is coupled to an external magnetic field.

6. The microfluidic chip of claim 1, wherein the granular particles are beads.

7. The microfluidic chip of claim 6, wherein the beads are magnetic or made of glass or cubic-zirconium.

8. The microfluidic chip of claim 1, further comprising a vent, a filter, a pouch or one or more additional chambers.

9. The microfluidic chip of claim 1, further comprising a thermal conductor, a thermal transducer or a thermal sensor.

10. The microfluidic chip of claim 8, wherein the pouch is made of polypropylene, polyethylene, polyethylene terephthalate (PET) or combinations thereof.

11. The microfluidic chip of claim 1, wherein the microfluidic chip is manufactured by using converted-tape technology.

12. The microfluidic chip of claim 1, wherein the chamber comprises at least one stir bar.

13. The microfluidic chip of claim 1, wherein the thermal device is in mechanical contact with the chamber.

14. The microfluidic chip of claim 1, further comprising a thermal transducer in thermal contact with the chamber.

15. The microfluidic chip of claim 1, wherein the thermal device is a heater.

16. The microfluidic chip of claim 1, wherein the thermal device is a resistive heater.

17. The microfluidic chip of claim 15, wherein the heater is attached to the chamber via an adhesive.

18. The microfluidic chip of claim 17, wherein the adhesive is heat conductive.

19. The microfluidic chip of claim 17, wherein the adhesive is pressure sensitive.

20. The microfluidic chip of claim 1, wherein the chamber comprises two chambers.

21. The microfluidic chip of claim 1, wherein a cross-section of the at least one insulative groove is not circular.

22. The microfluidic chip of claim 1, wherein the at least one insulative groove is less than 100 μm in length.

23. The microfluidic chip of claim 1, wherein the at least one insulative groove is less than 30 μm in width.

24. The microfluidic chip of claim 1, wherein the at least one insulative groove is greater than 0.001 μm in length.

* * * * *